US008304395B2

(12) United States Patent
Yedgar

(10) Patent No.: US 8,304,395 B2
(45) Date of Patent: Nov. 6, 2012

(54) LIPID CONJUGATES IN THE TREATMENT OF DISEASE

(75) Inventor: Saul Yedgar, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 603 days.

(21) Appl. No.: 11/822,423

(22) Filed: Jul. 5, 2007

(65) Prior Publication Data

US 2008/0293672 A1    Nov. 27, 2008

Related U.S. Application Data

(63) Continuation-in-part of application No. 10/989,606, filed on Nov. 17, 2004, now Pat. No. 7,811,999, and a continuation-in-part of application No. 10/952,496, filed on Sep. 29, 2004, now Pat. No. 7,393,938, which is a continuation-in-part of application No. 09/756,765, filed on Jan. 10, 2001, now Pat. No. 7,034,006.

(60) Provisional application No. 60/174,905, filed on Jan. 10, 2000, provisional application No. 60/174,907, filed on Jan. 10, 2000.

(51) Int. Cl.
*A61K 31/70* (2006.01)
*A61K 31/715* (2006.01)
*C08B 37/08* (2006.01)
*C08B 37/10* (2006.01)
*C07H 5/06* (2006.01)

(52) U.S. Cl. ............... 514/42; 514/53; 514/54; 514/56; 514/61; 514/62; 536/18.7; 536/20; 536/21; 536/22.1; 536/29.1; 536/29.13; 536/123.1

(58) Field of Classification Search .............. 514/42, 514/53, 54, 56, 61, 62; 536/18.7, 20, 21, 536/22.1, 29.1, 29.13, 123.1
See application file for complete search history.

(56) References Cited

U.S. PATENT DOCUMENTS

| | | | |
|---|---|---|---|
| 4,604,376 A | 8/1986 | Teng | |
| 4,624,919 A | 11/1986 | Kokusho | |
| 4,654,327 A | 3/1987 | Teng | |
| 5,064,817 A | 11/1991 | Yedgar et al. | |
| 5,169,636 A | 12/1992 | Nanba et al. | |
| 5,354,853 A | 10/1994 | Staveski | |
| 5,401,511 A | 3/1995 | Margalit | |
| 5,401,777 A | 3/1995 | Ammon et al. | |
| 5,464,942 A | 11/1995 | Sakurai et al. | |
| 5,470,578 A | 11/1995 | Aoki et al. | |
| 5,512,671 A | 4/1996 | Piantadose | |
| 5,587,363 A | 12/1996 | Henderson | |
| 5,707,821 A | 1/1998 | Rydel et al. | |
| 5,733,892 A | 3/1998 | Sakurai | |
| 5,785,975 A | 7/1998 | Parikh | |
| 6,022,866 A | 2/2000 | Falk et al. | |
| 6,043,231 A | 3/2000 | Pruzanski et al. | |
| 6,071,532 A | 6/2000 | Chaikof et al. | |
| 6,162,787 A | 12/2000 | Sorgente et al. | |
| 6,171,614 B1 | 1/2001 | Chaikof et al. | |
| 6,180,596 B1 | 1/2001 | Tsao | |
| 6,325,385 B1 | 12/2001 | Iwashita | |
| 6,749,813 B1 | 6/2004 | David | |
| 7,034,006 B2 | 4/2006 | Yedgar et al. | |
| 7,101,859 B2 | 9/2006 | Yedgar et al. | |
| 7,141,552 B2 | 11/2006 | Yedgar et al. | |
| 7,393,938 B2 | 7/2008 | Yedgar | |
| 7,504,384 B2 | 3/2009 | Yedgar et al. | |
| 7,608,598 B2 | 10/2009 | Yedgar | |

FOREIGN PATENT DOCUMENTS

| | | |
|---|---|---|
| EP | 0236951 | 9/1987 |
| EP | 0529659 | 3/1993 |
| EP | 0581281 | 2/1994 |
| EP | 0581282 B | 2/1994 |
| EP | 1046394 A | 10/2000 |
| JP | 04082893 | 3/1992 |
| JP | 09030970 | 2/1997 |
| JP | 09030979 | 2/1997 |
| JP | 2002345455 | 12/2002 |
| JP | 2003160498 | 3/2003 |
| JP | 2003335801 | 11/2003 |
| JP | 2004018841 | 1/2004 |
| JP | 2004170194 | 6/2004 |
| WO | WO 87/02777 | 5/1987 |
| WO | WO 91/00289 | 1/1991 |
| WO | WO 96/04001 | 2/1996 |
| WO | WO 96/11670 | 4/1996 |
| WO | WO 9628544 | 9/1996 |
| WO | WO 9701330 | 1/1997 |
| WO | WO 97/48337 | 12/1997 |
| WO | WO 9816198 | 4/1998 |
| WO | WO 98/51285 | 11/1998 |
| WO | WO 01/51003 | 7/2001 |
| WO | WO 01/91805 | 12/2001 |
| WO | WO 2005/084307 | 9/2005 |

OTHER PUBLICATIONS

Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" *Cancer Res* 47(12):3239-45.

Balsinde, J, Balboa, MA, Yedgar, S and Dennis, EA (2000) "Group V phospholipase A(2)-mediated oleic acid mobilization in lipopolysaccharide-stimulated P388D(1) macrophages" *J Biol Chem* 275(7):4783-6.

(Continued)

*Primary Examiner* — Peter G O'Sullivan

(74) *Attorney, Agent, or Firm* — Pearl Cohen Zedek Latzer, LLP; Mark S. Cohen

(57) ABSTRACT

The invention relates to methods of use for compounds in treating, reducing the incidence, reducing the severity or pathogenesis of an intestinal disease or condition in a subject, including, inter alia, inflammatory bowel disease, Crohn's disease, ulcerative colitis, or a combination thereof.

6 Claims, 9 Drawing Sheets

OTHER PUBLICATIONS

Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" *Br J Pharmacol* 135(7):1665-74.

Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" *J Neuroimmunol* 115(1-2):152-60.

Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein: identification with monoclonal antibody" *J Neurosci* 6(7):1925-33.

Brenner, T, Poradosu, E, Soffer, D, Sicsic, C, Gazit, A and Levitzki, A (1998) "Suppression of experimental autoimmune encephalomyelitis by tyrphostin AG-556" *Exp Neurol* 154(2):489-98.

Cabanas, C and Hogg, N (1993) "Ligand intercellular adhesion molecule 1 has a necessary role in activation of integrin lymphocyte function-associated molecule 1" *Proc Natl Acad Sci U S A* 90(12):5838-42.

Chen, WM, Soria, J, Soria, C, Krimsky, M and Yedgar, S (2002) "Control of capillary formation by membrane-anchored extracellular inhibitor of phospholipase A(2)" *FEBS Lett* 522(1-3):113-8.

Dan, P, Dagan, A, Krimsky, M, Pruzanski, W, Vadas, P and Yedgar, S (1998) "Inhibition of type I and type II phospholipase A2 by phosphatidyl-ethanolamine linked to polymeric carriers" *Biochemistry* 37(17):6199-204.

Darville, T, Yedgar, S, Krimsky, M, Andrews, CW, Jr., Jungas, T and Ojcius, DM (2004) "Protection against *Chlamydia trachomatis* infection in vitro and modulation of inflammatory response in vivo by membrane-bound glycosaminoglycans" *Microbes Infect* 6(4):369-76.

Davidson, FF, Dennis, EA, Powell, M and Glenney, JR, Jr. (1987) "Inhibition of phospholipase A2 by "lipocortins" and calpactins. An effect of binding to substrate phospholipids" *J Biol Chem* 262(4):1698-705.

Greaves MW and Camp RD (1988) "Prostaglandins, leukotrienes, phospholipase, platelet activating factor, and cytokines: an integrated approach to inflammation of human skin." *Arch Dermatol Res* 280:S33-41.

Krimsky, M, Dagan, A, Aptekar, L, Ligumsky, M and Yedgar, S (2000) "Assessment of intestinal permeability in rats by permeation of inulin-fluorescein" *J Basic Clin Physiol Pharmacol* 11(2):143-53.

Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" *Transfusion* 36(8):743-50.

Murthy, SN, Cooper, HS, Shim, H, Shah, RS, Ibrahim, SA and Sedergran, DJ (1993) "Treatment of dextran sulfate sodium-induced murine colitis by intracolonic cyclosporin" *Dig Dis Sci* 38(9):1722-34.

Okayasu, I, Hatakeyama, S, Yamada, M, Ohkusa, T, Inagaki, Y and Nakaya, R (1990) "A novel method in the induction of reliable experimental acute and chronic ulcerative colitis in mice" *Gastroenterology* 98(3):694-702.

Schmiel, DH and Miller, VL (1999) "Bacterial phospholipases and pathogenesis" *Microbes Infect* 1(13):1103-12.

Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Schnitzer, E, Pinchuk, I, Fainaru, M, Lichtenberg, D and Yedgar, S (1998) "LDL-associated phospholipase A does not protect LDL against lipid peroxidation in vitro" *Free Radic Biol Med* 24(7-8):1294-303.

Yard, BA, Yedgar, S, Scheele, M, Van Der Woude, D, Beck, G, Heidrich, B, Krimsky, M, Van Der Woude, FJ and Post, S (2002) "Modulation of IFN-gamma-induced immunogenicity by phosphatidylethanolamine-linked hyaluronic acid" *Transplantation* 73(6):984-92.

Yedgar, S, Lichtenberg, D and Schnitzer, E (2000) "Inhibition of phospholipase A(2) as a therapeutic target" *Biochim Biophys Acta* 1488(1-2):182-7.

Soeda et al (Biochemistry 29:5188-5144) Tissue Plasminogen Activator Catalyzed Lys-Plasminogen Activation on Heparin-Inserted Phospholipid Liposomes.

Parish et al (Int. J. Cancer 40: 511-518, "Evidence that sulphated polysaccharides inhibit tumour metastasis by blocking tumour-cell-derived heparanases."

Wang D.P, Matthias Schuster, Yi Fong Wang, Chi Huey Wong "Synthesis of phospholipid-inhibitor conjugates by enzymic transphosphatidylation with phospholipase", J. Am. Chem. Soc.; 1993; 115(23); 10487-10491.

Carey et al, "Contrasting effects of cycloxygenase-1 (cox-1) and cox-2 deficiency in the host response to influenze, a viral infection". Journ. of Immunology 2005, vol. 15: 175 (10): 6878-84.

Teitelbaum D, Arnon R, Sela M, Rabinsohn Y, Shapiro D., "Sphingomyelin specific antibodies elicited by synthetic conjugates," Immunochemistry. Nov. 1973;10(11):735-43.

Weltzien HU, Matthiessen HP, Meyer-Delius M, Zimmermann F, Rüde E., "Acidic "peptidophospholipids", a new class of hapten-bearing cell surface modifying reagents," Mol Immunol. Sep. 1984;21(9):801-10.

Winger TM, Ludovice PJ, Chaikof EL, "Lipopeptide conjugates: biomolecular building blocks for receptor activating membrane-mimetic structures," Biomaterials. Feb. 1996;17(4):437-41.

Office Action of U.S. Appl. No. 11/220,965 dated Mar. 27, 2008.
Office Action of U.S. Appl. No. 11/598,812 dated Dec. 19, 2008.
Office Action of U.S. Appl. No. 10/989,606 dated Sep. 1, 2009.
Supplementary Search Report of European Application No. 05724186.1 dated Nov. 17, 2009.
Ofice Action of Japanese Application No. 2001-551427 dated Nov. 20, 2009.
Cummings, B.S., "Phospholipase $A_2$ as targets for anti-cancer drugs," Biochemical Pharmacology 74 (2007), pp. 949-959.
Kokotos, G. et al., "Novel 2-Oxoamide Inhibitors of Human Group IVA Phospholipase $A_2$," J. Med. Chem., 2002, 45, pp. 2891-2893.
Extended European Search Report of European Application No. 05808267.8 issued Mar. 15, 2012.
Phyllis, Dan et al., "Inhibition of Type I and Type II Phospholipase A2 by Phosphatidyl-Ethanolamine Linked to Polymeric Carriers," Biochemistry, 1998, 37 (17), pp. 6199-6204.

LIPID CONJUGATES IN THE TREATMENT OF DISEASE

CROSS REFERENCE TO RELATED APPLICATIONS

This application is a continuation-in-part of U.S. patent application Ser. No. 10/989,606, filed on 17 Nov. 2004 now U.S. Pat. No. 7,811,999 and of U.S. patent application Ser. No. 10/952,496, filed on 29 Sep. 2004 now U.S. Pat. No. 7,393,938, which are continuations-in-part of U.S. application Ser. No. 09/756,765, filed Jan. 10, 2001 now U.S. Pat. No. 7,034,006 which claims the benefit of U.S. Provisional Application Ser. No. 60/174,905, filed Jan. 10, 2000, and U.S. Provisional Application Ser. No. 60/174,907 filed Jan. 10, 2000, which are incorporated in their entirety herein by reference.

FIELD OF THE INVENTION

This invention is directed to the treatment, reduction of incidence or severity of neoplasia in a subject, comprising administering to the subject a compound comprising a glycosaminoglycan conjugated on multiple uronic acid residues to a lipid or phospholipids, via amide linkages.

BACKGROUND OF THE INVENTION

Lipid-conjugates are thought to inhibit the enzyme phospholipase A2 (PLA2, EC 3.1.1.4). Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids. Lipid-conjugates may offer a wider scope of protection of cells and organisms from injurious agents and pathogenic processes, including the prevention and treatment of dermatologic conditions.

SUMMARY OF THE INVENTION

In some embodiments, this invention provides a method of reducing the incidence of neoplasia, reducing the severity of neoplasia, or treating neoplasia in a subject, delaying, reducing or abrogating cancer stage progression in a subject, prolonging latency in a subject suffering from cancer, or prolonging remission in a subject suffering from cancer, comprising the step of administering to said subject a compound represented by the structure of the general formula (A):

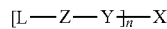

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
and/or a pharmaceutically acceptable salt or a pharmaceutical product thereof.

In one embodiment, the glycosaminoglycan is heparin, or in another embodiment,
In one embodiment, L is phosphatidylethanolamine, which in one embodiment is dipalmitoyl phosphatidylethanolamine, or in another embodiment, dimyristoyl phosphatidylethanolamine. In one embodiment, the In one embodiment, the subject suffers from a sarcoma. In another embodiment, the subject suffers from an adenocarcinoma, colon carcinoma, melanoma, breast carcinoma, leukemia, lymphoma, gastric carcinoma, glioblastoma, astrocytoma, bladder carcinoma, pleural mesothelioma, oat cell carcinoma or bronchogenic carcinoma. In one embodiment, this invention provides a method of reducing the incidence of, reducing the severity of or pathogenesis of cancer metastasis in a subject, comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
and/or a pharmaceutically acceptable salt or a pharmaceutical product thereof.

BRIEF DESCRIPTION OF THE DRAWINGS

Lipid-conjugates are thought to inhibit the enzyme phospholipase A2 (PLA2, EC 3.1.1.4). Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids. Lipid-conjugates may offer a wider scope of protection of cells and organisms from injurious agents and pathogenic processes, including the prevention and treatment of dermatologic conditions.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
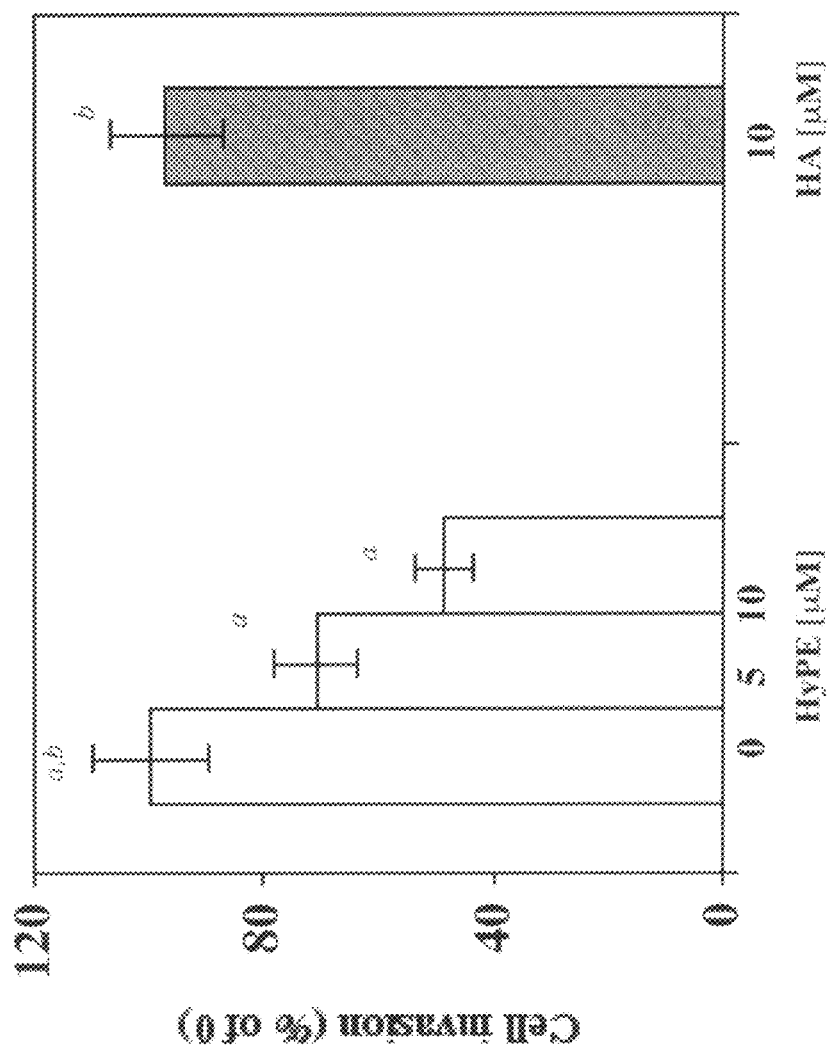
FIG. 1 describes the inhibition of HT-1080 cell invasion by sPLA$_2$ inhibitor. HT-1080 cells were treated with the extracellular sPLA$_2$ inhibitor (ExPLI) HyPE, composed of Hyaluronic acid (HA) conjugated PE and with HA alone, at the indicated concentrations, for 24 h, than washed and placed on a Matrigel membrane. Cell invasion through the Matrigel was determined as described in Materials and methods. Each datum is Mean and SD for 3 replications (a, b, P less then 0.05).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In some embodiments, this invention provides a method of reducing the incidence of neoplasia, reducing the severity of neoplasia, or treating neoplasia in a subject, delaying, reducing or abrogating cancer stage progression in a subject, prolonging latency in a subject suffering from cancer, or prolonging remission in a subject suffering from cancer, comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
and/or a pharmaceutically acceptable salt or a pharmaceutical product thereof.

(I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or a combination thereof. In one embodiment, this invention provides a method of reducing the incidence of, reducing the severity of or pathogenesis of cancer metastasis in a subject, comprising the step of administering to said subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
and/or a pharmaceutically acceptable salt or a pharmaceutical product thereof.

(I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or a combination thereof. In one embodiment, the glycosaminoglycan is heparin, or in another embodiment, In one embodiment, L is phosphatidylethanolamine, which in one embodiment is dipalmitoyl phosphatidylethanolamine, or in another embodiment, dimyristoyl phosphatidylethanolamine. In one embodiment, the Compounds In one embodiment, the compounds for use in the present invention comprise a lipid or phospholipid moiety bound to a physiologically acceptable monomer, dimer, oligomer, or polymer. In one embodiment, the physiologically acceptable monomer, dimer, oligomer, or polymer is salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, a dipeptide, a disaccharide, a trisaccharide, an oligosaccharide, a polysaccharide, a hetero-polysaccharide, a homo-polysaccharide, a polypyranose, an oligopeptide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid, a glycosaminoglycan, polygeline ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In one embodiment, examples of polymers which can be employed as the conjugated moiety for producing compounds for use in the methods of this invention may be physiologically acceptable polymers, including water-dispersible or -soluble polymers of various molecular weights and diverse chemical types, mainly natural and synthetic polymers, such as glycosaminoglycans, hyaluronic acids, heparin, heparin sulfates, chondroitin sulfates, chondroitin-6-sulfates, chondroitin-4-sulfates, keratins, keratin sulfates, dermatins, dermatan sulfates, dextrans, plasma expanders, including polygeline ("Haemaccel", degraded gelatin polypeptide cross-linked via urea bridges, produced by "Behring"), "hydroxyethylstarch" (Hetastarch, HES) and extrans, food and drug additives, soluble cellulose derivatives (e.g., methylcellulose, carboxymethylcellulose), polyaminoacids, hydrocarbon polymers (e.g., polyethylene), polystyrenes, polyesters, polyamides, polyethylene oxides (e.g. polyethyleneglycols, polycarboxyethyleneglycols, polycarboxylated polyethyleneglycols), polyvinnylpyrrolidones, polysaccharides, polypyranoses, alginates, assimilable gums (e.g., xanthan gum), peptides, injectable blood proteins (e.g., serum albumin), cyclodextrin, and derivatives thereof.

In one embodiment, examples of monomers, dimers, and oligomers which can be employed as the conjugated moiety for producing compounds for use in the present invention for use in the methods of the invention may be mono- or disaccharides, trisaccharides, oligopeptides, carboxylic acids, dicarboxylic acids, fatty acids, dicarboxylic fatty acids, salicylates, slicyclic acids, acetyl salicylic acids, aspirins, lactobionic acids, maltoses, amino acids, glycines, glutaric acids, succinic acids, dodecanoic acids, didodecanoic acids, bile acids, cholic acids, cholesterylhemisuccinates, and di- and trisaccharide unit monomers of polysaccharides, polypyranoses, and/or glycosaminoglycans including heparins, heparan sulfates, hyaluronic acids, chondroitins, chondroitin sulfates, chondroitin-6-sulfates, chondroitin-4-sulfates, dermatins, dermatan sulfates, keratins, keratan sulfates, or dextrans.

In one embodiment, the lipid compounds for use in the present invention are described by the general formula:
[phosphatidylethanolamine-Y]n-X
[phosphatidylserine-Y]n-X
[phosphatidylcholine-Y]n-X
[phosphatidylinositol-Y]n-X
[phosphatidylglycerol-Y]n-X
[phosphatidic acid-Y]n-X
[lyso-phospholipid-Y]n-X
[diacyl-glycerol-Y]n-X
[monoacyl-glycerol-Y]n-X
[sphingomyelin-Y]n-X
[sphingosine-Y]n-X
[ceramide-Y]n-X
wherein
Y is either nothing or a spacer group ranging in length from 2 to 30 atoms; and
X is a physiologically acceptable monomer, dimer, oligomer or polymer; and
n is the number of lipid molecules bound to a molecule of X, wherein n is a number from 1 to 1000.

In one embodiment, the invention provides low-molecular weight compounds, previously undisclosed and unknown to possess pharmacological activity, of the general formula described hereinabove. In another embodiment, wherein the general formula described hereinabove describes low-molecular weight compounds, X is a mono- or di-saccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid.

In one embodiment of this invention, X is any of the physiologically acceptable monomer, dimer, oligomer, or polymer, as described herein. In one embodiment, X is conjugated to the lipid, phospholipid, or spacer via an ester bond. In another embodiment, X is conjugated to the lipid, phospholipid, or spacer via an amide bond.

As defined by the structural formulae provided herein for the compounds for use in the present invention, these compounds may contain between one to one thousand lipid moieties bound to a single physiologically acceptable polymer molecule. In one embodiment of this invention, n is a number from 1 to 1000. In another embodiment, n is a number from 1 to 500. In another embodiment, n is a number from 1 to 100. In another embodiment, n is a number from 2 to 1000. In another embodiment, n is a number from 2 to 100. In another embodiment, n is a number from 2 to 200. In another embodiment, n is a number from 3 to 300. In another embodiment, n is a number from 10 to 400. In another embodiment, n is a number from 50 to 500. In another embodiment, n is a number from 100 to 300. In another embodiment, n is a number from 300 to 500. In another embodiment, n is a number from 500 to 800. In another embodiment, n is a number from 500 to 1000.

In one embodiment of the invention, when the conjugated moiety is a polymer, the ratio of lipid moieties covalently bound may range from one to one thousand lipid residues per polymer molecule, depending upon the nature of the polymer and the reaction conditions employed. For example, the relative quantities of the starting materials, or the extent of the reaction time, may be modified in order to obtain products with either high or low ratios of lipid residues per polymer, as desired.

In one embodiment, the set of compounds comprising phosphatidylethanolamine covalently bound to a physiologically acceptable monomer, dimmer, oligomer, or polymer, is referred to herein as the PE-conjugates. In one embodiment, the phosphatidylethanolamine moiety is dipalmitoyl phosphatidylethanolamine. In another embodiment, the phosphatidylethanolamine moiety is dimyristoyl phosphatidylethanolamine. In another embodiment, related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the structural similarities shared by these compounds.

In another embodiment, the lipid or phospholipid moiety is phosphatidic acid, an acyl glycerol, monoacylglycerol, diacylglycerol, triacylglycerol, sphingosine, sphingomyelin, chondroitin-4-sulfate, chondroitin-6-sulfate, ceramide, phosphatidylethanolamine, phosphatidylserine, phosphatidylcholine, phosphatidylinositol, or phosphatidylglycerol, or an ether or alkyl phospholipid derivative thereof.

In one embodiment, derivatives relevant to this invention are compounds wherein at least one of the fatty acid groups of the lipid moieties at position C1 or C2 of the glycerol backbone are substituted by a long chain alkyl group attached by amide, ether or alkyl bonds, rather than ester linkages.

In the methods, according to embodiments of the invention, the compounds for use in the present invention administered to the subject are comprised from at least one lipid moiety covalently bound through an atom of the polar head group to a monomeric or polymeric moiety (referred to herein as the conjugated moiety) of either low or high molecular weight. When desired, an optional bridging moiety can be used to link the compounds for use in the present invention moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or di-saccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondroitin-sulfate, dermatan, keratan sulfate, or a higher molecular weight peptide or oligopeptide, a polysaccharide, a hetero-polysaccharide, a homo-polysaccharide, a polypyranose, polyglycan, protein, glycosaminoglycan, or a glycoprotein mixture. The composition of some phospholipid-conjugates of high molecular weight, and associated analogues, are the subject of U.S. Pat. No. 5,064,817, which is incorporated herein in its entirety by reference.

In one embodiment, the term "moiety" means a chemical entity otherwise corresponding to a chemical compound, which has a valence satisfied by a covalent bond.

In some cases, according to embodiments of the invention, the monomer or polymer chosen for preparation of the compound may in itself have select biological properties. For example, both heparin and hyaluronic acid are materials with known physiological functions. In the present invention, however, the compounds for use in the present invention formed from these substances as starting materials display a new and wider set of pharmaceutical activities than would be predicted from administration of either heparin or hyaluronic acid which have not been bound by covalent linkage to a phospholipid. In some embodiments, phosphatidylethanolamine (PE) linked to hyaluronic acid (Compound XXII), to heparin (Compound XXIV), to chondroitin sulfate A (Compound XXV), to carboxymethylcellulose (Compound XXVI), to Polygeline (haemaccel) (Compound XXVII), to alginate (Compound LI), or to hydroxyethylstarch (Compound XXVIII), are useful for methods and in compositions as herein described but perform unexpectedly in terms of potency and range of useful pharmaceutical activity compared to the free conjugates. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone. In one embodiment, such properties may include: greater local persistence, greater anti-inflammatory properties, greater antioxidant activity, or a combination thereof.

The biologically active compounds for use in the present invention described herein can have a wide range of molecular weights, e.g., above 50,000 (up to a few hundred thousands) when it is desirable to retain the Lipid conjugate in the vascular system and below 50,000 when targeting to extravascular systems is desirable. The sole limitation on the molecular weight and the chemical structure of the conjugated moiety is that it does not result in a compound devoid of the desired biological activity, or lead to chemical or physiological instability to the extent that the Compound is rendered useless as a drug in the method of use described herein.

In one embodiment, the compound for use in the present invention is represented by the structure of the general formula (A):

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between L, Z, Y and X is either an amide or an esteric bond.

In one embodiment, L is phosphatidyl, Z is ethanolamine, wherein L and Z are chemically bonded resulting in phosphatidylethanolamine, Y is nothing, and X is carboxymethylcellulose. In another embodiment, L is phosphatidyl, Z is ethanolamine, wherein L and Z are chemically bonded resulting in phosphatidylethanolamine, Y is nothing, and X is a glycosaminoglycan. In one embodiment, the phosphatidylethanolamine moiety is dipalmitoyl phosphatidylethanolamine. In another embodiment, the phosphatidylethanolamine moiety is dimyristoyl phosphatidylethanolamine.

In another embodiment, the compound for use in the present invention is represented by the structure of the general formula (I):

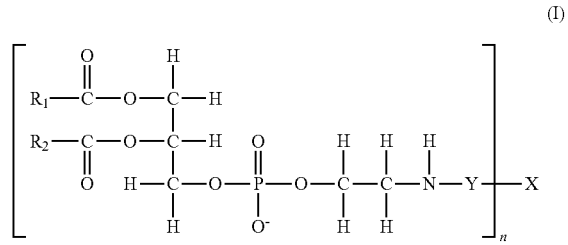

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is either a physiologically acceptable monomer, dimer, oligomer or a physiologically acceptable polymer; and n is a number from 1 to 1,000;

wherein if Y is nothing the phosphatidylethanolamine is directly linked to X via an amide bond and if Y is a spacer, the spacer is directly linked to X via an amide or an esteric bond and to the phosphatidylethanolamine via an amide bond.

In one embodiment, compounds for use in the methods of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethyl-cellulose, heparin, hyaluronic acid, chondroitin sulfate, polygeline (haemaccel), hydroxyethylstarch (Hetastarch, HES) polyethyleneglycol, polycarboxylated polyethylene glycol, a glycosaminoglycan, a polysaccharide, a hetero-polysaccharide, a homo-polysaccharide, or a polypyranose. The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. In one embodiment, the PE moiety is dipalmitoyl-phosphatidyl-ethanolamine. In another embodiment, the PE moiety is dimyristoyl-phosphatidyl-ethanolamine.

Phosphatidyl-ethanolamine and its analogues may be from various sources, including natural, synthetic, and semisynthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylseline (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), phosphatidic acid and phosphoatidylglycerol (PG), as well as derivatives thereof comprising either phospholipids, lysophospholipids, phosphatidic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, the compound for use in the present invention is represented by the structure of the general formula (II):

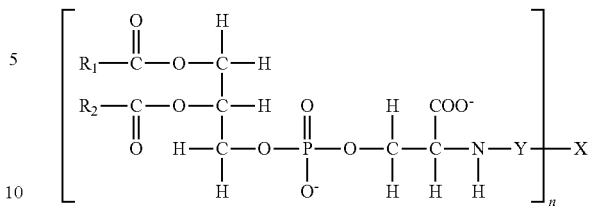

(II)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a glycosaminoglycan; and n is a number from 1 to 1000;

wherein if Y is nothing, the phosphatidylserine is directly linked to X via an amide bond and if Y is a spacer, the spacer is directly linked to X via an amide or an esteric bond and to the phosphatidylserine via an amide bond.

In one embodiment, the phosphatidylserine may be bonded to Y, or to X if Y is nothing, via the $COO^-$ moiety of the phosphatidylserine.

In another embodiment, the compound for use in the present invention is represented by the structure of the general formula (III):

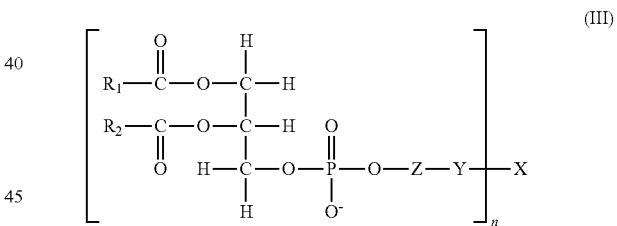

(III)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phosphatidyl, Z, Y and X is either an amide or an esteric bond.

In another embodiment, the compound for use in the present invention is represented by the structure of the general formula (IV):

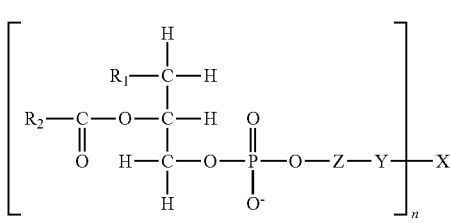

(IV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (V):

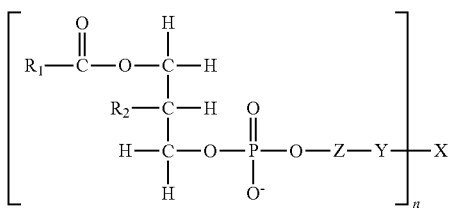

(V)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (VI):

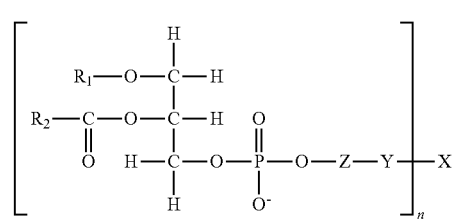

(VI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (VII):

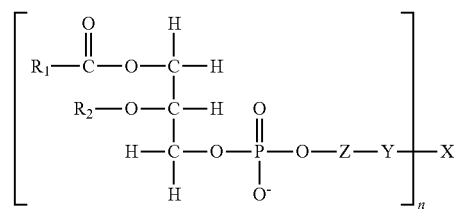

(VII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In one embodiment of the invention, phosphatidylcholine (PC), phosphatidylinositol (PI), phosphatidic acid (PA), wherein Z is nothing, and phosphatidylglycerol (PG) conjugates are herein defined as compounds of the general formula (III).

In another embodiment, the compound for use in the present invention is represented by the structure of the general formula (VIII):

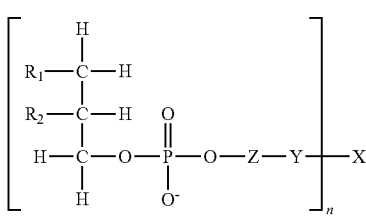

(VIII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (IX):

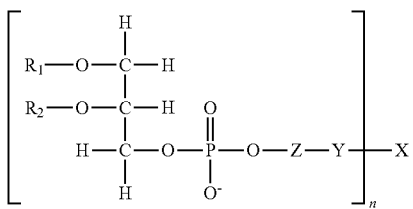

(IX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (IXa):

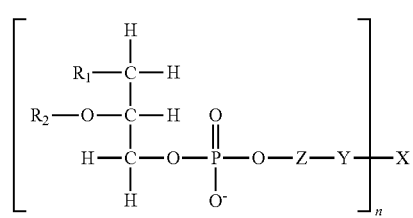

(IXa)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (IXb):

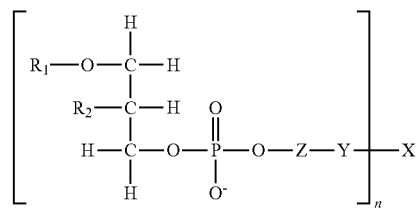

(IXb)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolanine, serine, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (X):

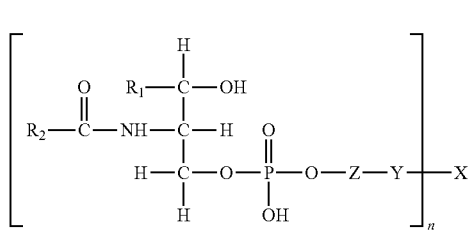
(X)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the ceramide phosphoryl, Z, Y and X is either an amide or an esteric bond.

In another embodiment, the compound for use in the present invention is represented by the structure of the general formula (XI):

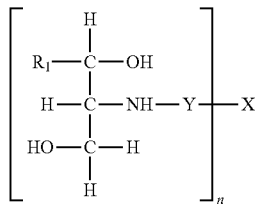
(XI)

wherein $R_1$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a glycosarminoglycan; and n is a number from 1 to 1000;

wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the compound for use in the present invention is represented by the structure of the general formula (XII):

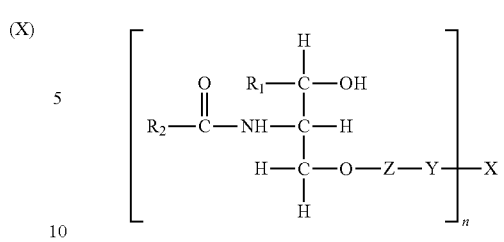
(XII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the ceramide, Z, Y and X is either an amide or an esteric bond.

In another embodiment, the compound for use in the present invention is represented by the structure of the general formula (XIII):

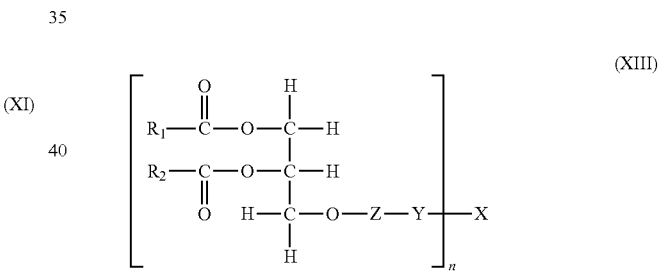
(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the diglyceryl, Z, Y and X is either an amide or an esteric bond.

In another embodiment, the compound for use in the present invention is represented by the structure of the general formula (XIV):

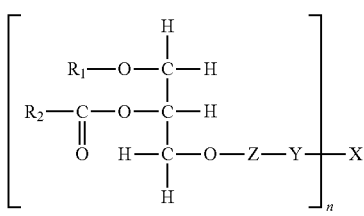

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the glycerolipid, Z, Y and X is either an amide or an esteric bond.

In another embodiment, the compound for use in the present invention is represented by the structure of the general formula (XV):

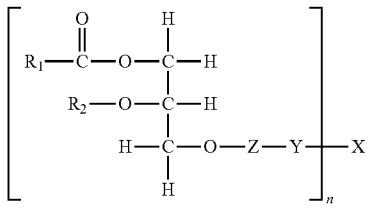

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the glycerolipid, Z, Y and X is either an amide or an esteric bond.

In another embodiment, the compound for use in the present invention is represented by the structure of the general formula (XVI):

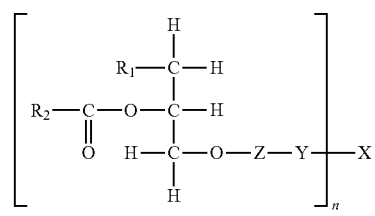

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XVII):

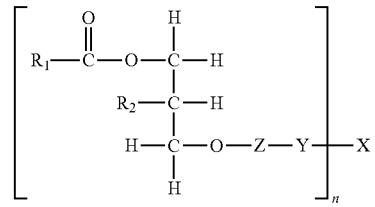

(XVII)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XVIII):

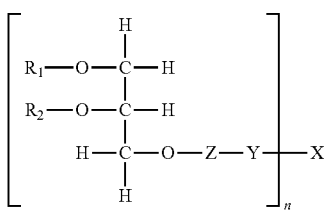

(XVIII)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XIX):

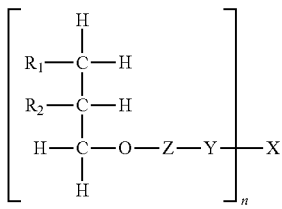

(XIX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XX):

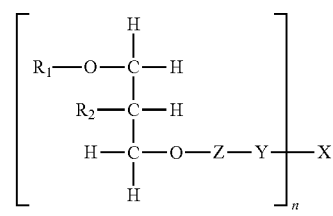

(XX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XXI):

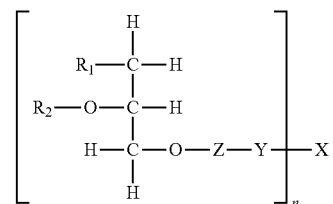

(XXI)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

For any or all of the compounds represented by the structures of the general formulae (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), and (XXII) hereinabove: In one embodiment, X is a glycosaminoglycan. According to this aspect and in one embodiment, the glycosaminoglycan may be, inter alia, hyaluronic acid, heparin, heparan sulfate, chondroitin sulfate, keratin, keratan sulfate, dermatan sulfate or a derivative thereof. In another embodiment, X is not a glycosaminoglycan. In another embodiment, X is a polysaccharide, which in one embodiment is a hetero-polysaccharide, and in another embodiment, is a homo-polysaccharide. In another embodiment, X is a polypyranose.

In another embodiment, the glycosaminoglycan is a polymer of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, m is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In another embodiment, the chondroitin sulfate may be, inter alia, chondroitin-6-sulfate, chondroitin-4-sulfate or a derivative thereof.

In one embodiment of the invention, Y is nothing. Non-limiting examples of suitable divalent groups forming the optional bridging group (which in one embodiment, is referred to as a spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene-NH—, —NH-alkylene-NH, CO-alkylene-NH—, an amino acid, cycloalkylene, wherein alkylene in each instance, is straight or branched chain and contains 2 or more, preferably 2 to 30 atoms in the chain, —(—O—CH(CH$_3$)CH$_2$—)$_x$— wherein x is an integer of 1 or more.

According to embodiments of the invention, in addition to the traditional phospholipid structure, related derivatives for use in this invention are phospholipids modified at the C1 or C2 position to contain an amine, ether or alkyl bond instead of an ester bond. In one embodiment of the invention, the alkyl phospholipid derivatives and ether phospholipid derivatives are exemplified herein.

In one embodiment of the invention, the sugar rings of the glycosaminoglycan are intact. In another embodiment, intact refers to closed. In another embodiment, intact refers to natural. In another embodiment, intact refers to unbroken.

In one embodiment of the invention, the structure of the lipid or phospholipid in any compound according to the invention is intact. In another embodiment, the natural structure of the lipid or phospholipids in any compound according to the invention is maintained.

In one embodiment, the compounds for use in the present invention are biodegradable.

In one embodiment, the compound according to the invention is phosphatidylethanolamine bound to aspirin. In one embodiment, the compound according to the invention is phosphatidylethanolamine bound to glutarate.

In some embodiments, the compounds for use are as listed in Table 1 below.

TABLE 1

| Phospholipid | Spacer | Polymer (m.w.) | Compound |
|---|---|---|---|
| PE | None | Hyaluronic acid (2-2000 kDa) | XXII |
| Dimyristoyl-PE | None | Hyaluronic acid | XXIII |
| PE | None | Heparin (0.5-110 kDa) | XXIV |
| PE | None | Chondroitin sulfate A | XXV |
| PE | None | Carboxymethylcellulose (20-500 kDa) | XXVI |
| PE | Dicarboxylic acid + Diamine | Polygeline (haemaccel) (4-40 kDa) | XXVII |
| PE | None | Hydroxyethylstarch | XXVIII |
| PE | Dicarboxylic acid + Diamine | Dextran (1-2,000 kDa) | XXIX |
| PE | None | Aspirin | XXX |
| PE | Carboxyl amino group | Hyaluronic acid (2-2000 kDa) | XXXI |
| PE | Dicarboxyl group | Hyaluronic acid (2-2000 kDa) | XXXII |
| PE | Dipalmitoic acid | Hyaluronic acid (2-2000 kDa) | XXXIII |
| PE | Carboxyl amino group | Heparin (0.5-110 kDa) | XXXIV |
| PE | Dicarboxyl group | Heparin (0.5-110 kDa) | XXXV |
| PE | Carboxyl amino group | Chondroitin sulfate A | XXXVI |
| PE | Dicarboxyl group | Chondroitin sulfate A | XXXVII |
| PE | Carboxyl amino group | Carboxymethylcellulose (20-500 kDa) | XXXVIII |
| PE | Dicarboxyl group | Carboxymethylcellulose (20-500 kDa) | XXXIX |
| PE | None | Polygeline (haemaccel) (4-40 kDa) | XL |
| PE | Carboxyl amino group | Polygeline (haemaccel) (4-40 kDa) | XLI |
| PE | Dicarboxyl group | Polygeline (haemaccel) (4-40 kDa) | XLII |
| PE | Carboxyl amino group | Hydroxyethylstarch | XLIII |
| PE | Dicarboxyl group | Hydroxyethylstarch | XLIV |
| PE | None | Dextran (1-2,000 kDa) | XLV |
| PE | Carboxyl amino group | Dextran (1-2,000 kDa) | XLVI |
| PE | Dicarboxyl group | Dextran (1-2,000 kDa) | XLVII |
| PE | Carboxyl amino group | Aspirin | XLVIII |
| PE | Dicarboxyl group | Aspirin | XLIX |
| PE | None | Albumin | L |
| PE | None | Alginate (2-2000 kDa) | LI |
| PE | None | Polyaminoacid | LII |
| PE | None | Polyethylene glycol | LIII |
| PE | None | Lactobionic acid | LIV |
| PE | None | Acetylsalicylate | LV |
| PE | None | Cholesteryl-hemmisuccinate | LVI |
| PE | None | Maltose | LVII |
| PE | None | Cholic acid | LVIII |
| PE | None | Chondroitin sulfates | LIX |
| PE | None | Polycarboxylated polyethylene glycol | LX |
| Dipalmitoyl-PE | None | Hyaluronic acid | LXI |

TABLE 1-continued

| Phospholipid | Spacer | Polymer (m.w.) | Compound |
|---|---|---|---|
| Dipalmitoyl-PE | None | Heparin | LXII |
| Dipalmitoyl-PE | None | Chondroitin sulfate A | LXIII |
| Dipalmitoyl-PE | None | Carboxymethylcellulose | LXIV |
| Dipalmitoyl-PE | None | Polygeline (haemaccel) | LXV |
| Dipalmitoyl-PE | None | Hydroxyethylstarch | LXVI |
| Dipalmitoyl-PE | None | Dextran | LXVII |
| Dipalmitoyl-PE | None | Aspirin | LXVIII |
| Dimyristoyl-PE | None | Heparin | LXVIX |
| Dimyristoyl-PE | None | Chondroitin sulfate A | LXX |
| Dimyristoyl-PE | None | Carboxymethylcellulose | LXXI |
| Dimyristoyl-PE | None | Polygeline (haemaccel) | LXXII |
| Dimyristoyl-PE | None | Hydroxyethylstarch | LXXIII |
| Dimyristoyl-PE | None | Dextran | LXXIV |
| Dimyristoyl-PE | None | Aspirin | LXXV |
| PS | None | Hyaluronic acid | LXXVI |
| PS | None | Heparin | LXXVII |
| PS | None | Polygeline (haemaccel) | LXXVIII |
| PC | None | Hyaluronic acid | LXXIX |
| PC | None | Heparin | LXXX |
| PC | None | Polygeline (haemaccel) | LXXXI |
| PI | None | Hyaluronic acid | LXXXII |
| PI | None | Heparin | LXXXIII |
| PI | None | Polygeline (haemaccel) | LXXXIV |
| PG | None | Hyaluronic acid | LXXXV |
| PG | None | Heparin | LXXXVI |
| PG | None | Polygeline (haemaccel) | LXXXVII |
| PE | None | Glutaryl | LXXXVIII |
| Dipalmitoyl-PE | None | Alginate | LXXXIX |
| Dimyristoyl-PE | None | Alginate | XC |
| PS | None | Alginate | XCI |
| PC | None | Alginate | XCII |
| PI | None | Alginate | XCIII |
| PG | None | Alginate | XCIV |
| PS | None | Hydroxyethylstarch | XCV |
| PC | None | Hydroxyethylstarch | XCVI |
| PI | None | Hydroxyethylstarch | XCVII |
| PG | None | Hydroxyethylstarch | XCVIII |
| PE | —CO—(CH$_2$)$_3$—CO—NH—(CH$_2$)$_6$— | Hydroxyethylstarch | XCIX |
| PE | —CO—CH$_2$— | Carboxymethylcellulose | C |

In one embodiment of the invention, the compounds for use in the present invention are any one or more of Compounds I-C. In another embodiment, the invention provides a composition comprising any combination of any of the compounds of the invention or the use of any combination of any of the compounds of the invention. In another embodiment, the compounds for use in the present invention are Compound XXII, Compound XXIII, Compound XXIV, Compound XXV, Compound XXVI, Compound XXVII, Compound XXVIII, Compound XXIX, Compound XXX, Compound LI, or pharmaceutically acceptable salts thereof, in combination with a physiologically acceptable carrier or solvent. According to embodiments of the invention, these polymers, when chosen as the conjugated moiety, may vary in molecular weights from 200 to 2,000,000 Daltons. In one embodiment of the invention, the molecular weight of the polymer as referred to herein is from 200 to 1000 Daltons. In another embodiment, the molecular weight of the polymer as referred to herein is from 200 to 1000 Daltons. In another embodiment, the molecular weight of the polymer as referred to herein is from 1000 to 5000 Daltons. In another embodiment, the molecular weight of the polymer as referred to herein is from 5000 to 10,000 Daltons. In another embodiment, the molecular weight of the polymer as referred to herein is from 10,000 to 20,000 Daltons. In another embodiment, the molecular weight of the polymer as referred to herein is from 10,000 to 50,000 Daltons. In another embodiment, the molecular weight of the polymer as referred to herein is from 20,000 to 70,000 Daltons. In another embodiment, the molecular weight of the polymer as referred to herein is from 50,000 to 100,000 Daltons. In another embodiment, the molecular weight of the polymer as referred to herein is from 100,000 to 200,000 Daltons. In another embodiment, the molecular weight of the polymer as referred to herein is from 200,000 to 500,000 Daltons. In another embodiment, the molecular weight of the polymer as referred to herein is from 200,000 to 1,000,000 Daltons. In another embodiment, the molecular weight of the polymer as referred to herein is from 500,000 to 1,000,000 Daltons. In another embodiment, the molecular weight of the polymer as referred to herein is from 1,000,000 to 2,000,000 Daltons. Various molecular weight species have been shown to have the desired biological efficacy.

In one embodiment, "approximately" refers to up to 5%, 10%, 15%, 20%, or 25% of the value. In another embodiment, "approximately" refers to 5-25%, 5-15%. 10-25%, 10-20%, 15-25% of the value.

In one embodiment of this invention, low molecular weight compounds for use in the present invention are defined hereinabove as the compounds of formula (I)-(XXI) wherein X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhernmisuccinate, a di- or tripeptide, an oligopeptide, a trisacharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid, glycosaminoglycan, or polypyranose.

Examples of suitable divalent groups forming the optional bridging group Y are straight- or branched-chain alkylene, e.g., of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—CH(CH$_3$)CH$_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VII) and (IX).

In one embodiment of the invention, X is covalently conjugated to a lipid. In another embodiment, X is covalently conjugated to a lipid via an amide bond. In another embodiment, X is covalently conjugated to a lipid via an esteric bond. In another embodiment, the lipid is phosphatidylethanolamine.

In one embodiment, the compound comprises a glycosaminoglycan, conjugated to a phosphatidylethanolamine via direct amide linkage. In one embodiment, according to this aspect, at least two or more phosphatidylethanolamines are linked to the glycosaminoglycan. In some embodiments, the compounds of this invention comprise amide linkages to 5-10 phosphatidylethanolamine to the glycosaminoglycan via linkage to uronic acid residues on the GAG. In some embodiments, the compounds of this invention comprise amide linkages to 3-5 phosphatidylethanolamine to the glycosaminoglycan via linkage to uronic acid residues on the GAG. In some embodiments, the compounds of this invention comprise amide linkages to 10-15 phosphatidylethanolamine to the glycosaminoglycan via linkage to uronic acid residues on the GAG. In some embodiments, the compounds of this invention comprise amide linkages to 15-20 phosphatidylethanolamine to the glycosaminoglycan via linkage to uronic acid residues on the GAG. In some embodiments, the compounds of this invention comprise amide linkages to 5-15 phosphatidylethanolamine to the glycosaminoglycan via linkage to uronic acid residues on the GAG. In some embodiments, the compounds of this invention comprise amide linkages to 3-10 phosphatidylethanolamine to the glycosaminoglycan via linkage to uronic acid residues on the GAG.

In another embodiment, a GAG-mimicking molecule may be, inter alia, a negatively charged molecule. In another embodiment, a GAG-mimicking molecule may be, inter alia, a salicylate derivative. In another embodiment, a GAG-mimicking molecule may be, inter alia, a dicarboxylic acid.

In another embodiment, the invention provides a pharmaceutical composition for treating a subject suffering from an intestinal disease, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from an intestinal disease, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII), or any combination thereof.

The combination of lipids, such as, but not limited to phosphatidylethanolamine and phosphatidylserine, with additional monomer or polymer moieties, is thus a practical route to the production of new drugs for medical purposes, provided that the resultant chemical composition displays the desired range of pharmacological properties. In one embodiment, the compounds for use in the present invention possess a combination of multiple and potent pharmacological effects in addition to the ability to inhibit the extracellular form of the enzyme phospholipase A2. While the pharmacological activity of the compounds for use in the present invention described herein may be due in part to the nature of the lipid moiety, the multiple and diverse combination of pharmacological properties observed for the compounds for use in the present invention emerges from the ability of the compound structure to act essentially as several different drugs in one chemical entity.

In the cases described herein, the diversity of biological activities and the effectiveness in disease exhibited by the compounds for use in the present invention far exceed the properties anticipated by use of the starting materials themselves, when administered alone or in combination. However, the phospholipid conjugate compounds, alone or in combination, are valuable when used in the methods of treating diseases and conditions specifically described herein.

Preparation of Compounds for Use in the Present Invention

In one embodiment, the preparation of high molecular weight compounds for use in the methods of the present invention is as described in U.S. Pat. No. 5,064,817, which is incorporated fully herein by reference. In one embodiment, these synthetic methods are applicable to the preparation of low molecular weight compounds for use in the present invention as well, i.e. compounds for use in the present invention comprising monomers and dimers as the conjugated moiety, with appropriate modifications in the procedure as would be readily evident to one skilled in the art. The preparation of some low molecular weight compounds for use in the present invention may be conducted using methods well known in the art or as described in U.S. patent application Ser. No. 10/952,496, which is incorporated herein by reference in its entirety.

Dosages and Routes of Administration

This invention encompasses administration of compounds as described herein or compositions comprising the same, for treating intestinal diseases.

In one embodiment, compositions of this invention are pharmaceutically acceptable. In one embodiment, the term "pharmaceutically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration.

In some embodiments, any of the compositions of this invention will comprise a compound of the present invention, in any form or embodiment as described herein. In some embodiments, any of the compositions of this invention will consist of a compound of the present invention, in any form or embodiment as described herein. In some embodiments, the compositions of this invention will consist essentially of a compound of the present invention, in any form or embodiment as described herein. In some embodiments, the term "comprise" refers to the inclusion of the indicated active agent, such as the Compounds (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII) or a combination thereof, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient. In one embodiment, a Compound used in the methods of this invention may be administered alone or within a composition. In another embodiment, compositions comprising compounds for use in the present invention in admixture with conventional excipients, i.e. pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

In one embodiment, the therapeutic compositions of the instant invention comprise a compound of the instant invention and additional compounds effective in preventing or treating aspects of carcinogenesis.

In one embodiment, the therapeutic compositions of the instant invention are administered with other treatments that relieve symptoms.

In one embodiment, the route of administration may be parenteral, enteral, or a combination thereof. In another embodiment, the route may be intra-ocular, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation, nasal aspiration (spray), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, etc.

For parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

For application by inhalation, solutions or suspensions of the compounds mixed and aerosolized or nebulized in the presence of the appropriate carrier suitable. Such an aerosol may comprise any agent described herein and, in one embodiment, may be used to treat diseases or conditions caused by airborne pathogens, which may in one embodiment, cause intestinal disorders.

For topical application, an admixture of the compounds with conventional creams, lotions, or delayed release patches is acceptable. Such a cream or lotion may comprise any agent described herein, and, in one embodiment, may be used to treat an intestinal disease.

For enteral application, particularly suitable are tablets, dragees, liquids, drops, or capsules. A syrup, elixir, or the like can be used when a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Thus, in one embodiment, the route of administration may be directed to an organ or system that is affected by an intestinal disease. For example, compounds may be administered intra-tumorally. In another embodiment, the route of administration may be directed to a different organ or system than the one that is affected by the original neoplasia, such as for example, treating metastasis to a secondary site. In some embodiments, compounds may be administered intravenously to provide for greater perfusion of the compound. Thus, the present invention provides for the use of compounds of the instant invention in various dosage forms suitable for administration using any of the routes listed hereinabove.

In general, the doses utilized for the above described purposes will vary, but will be in an effective amount to exert the desired effect. As used herein, the term "pharmaceutically effective amount" refers to an amount of a compound of formulae A and I—C as described hereinabove, which will produce the desired alleviation in symptoms or other desired phenotype in a patient. The doses utilized for any of the above-described purposes will generally be from 1 to about 1000 milligrams per kilogram of body weight (mg/kg), administered one to four times per day, or by continuous IV infusion. In one embodiment, compounds may be administered at a concentration of 5 mg/ml, while in another embodiment, compounds may be administered at a concentration of 20 mg/ml. In another embodiment, compounds may be administered at 1, 2, 3, 4, 7, 10, 12, 15, 17, or 25 mg/ml. In one embodiment, compounds may be administered by gavage, while in another embodiment, they may be administered orally. In one embodiment, compounds are administered three times per day, while in another embodiment, compounds are administered continuously, such as via drinking water or intravenous feed. In another embodiment, compounds are administered once per day, and in another embodiment, two times per day, four times per day or five times per day.

When the compositions are dosed topically or intraocularly, they will generally be in a concentration range of from 0.1 to about 10% w/v, administered 1-4 times per day.

In one embodiment of the invention, the concentrations of the compounds will depend on various factors, including the nature of the condition to be treated, the condition of the patient, the route of administration and the individual tolerability of the compositions.

It will be appreciated that the actual preferred amounts of active compound in a specific case will vary according to the specific compound being utilized, the particular compositions formulated, the mode of application, and the particular conditions and organism being treated. Dosages for a given host can be determined using conventional considerations, e.g., by customary comparison of the differential activities of the subject compounds and of a known agent, e.g., by means of an appropriate, conventional pharmacological protocol.

In one embodiment, the compounds of the invention may be administered acutely for acute treatment of temporary conditions, or may be administered chronically, especially in the case of progressive, recurrent, or degenerative disease. In one embodiment, one or more compounds of the invention may be administered simultaneously, or in another embodiment, they may be administered in a staggered fashion. In one embodiment, the staggered fashion may be dictated by the stage or phase of the disease.

In one embodiment, the present invention offers methods for the treatment of disease based upon administration of lipids covalently conjugated through their polar head group to a physiologically acceptable chemical moiety, which may be of high or low molecular weight.

In some embodiments, this invention provides methods of use which comprise administering a composition comprising the described compounds. As used herein, "pharmaceutical composition" means a "therapeutically effective amount" of the active ingredient, i.e. compounds as herein described, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compounds as herein described. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The pharmaceutical compositions containing the compounds as herein described can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitonealy, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the compounds as herein described are formulated in a capsule. In accordance with this embodiment, the compositions of the present invention comprise in addition to the compounds as herein described and the inert carrier or diluent, a hard gelatin capsule.

In one embodiment, the micronized capsules comprise particles containing compounds as herein described, wherein the term "micronized" used herein refers to particles having a particle size is of less than 100 microns, or in another embodiment, less than 50 microns, or in another embodiment, less than 35 microns, or in another embodiment, less than 15 microns, or in another embodiment, less than 10 microns, or in another embodiment, less than 5 microns.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds as herein described or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of the compounds as herein described over a period of time. In a further embodiment, the pharmaceutical compositions are administered intravaginally.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formuations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In one embodiment, the compositions of this invention may include, a compound of this invention or any combination thereof, together with one or more pharmaceutically acceptable excipients.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or -non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sobitan esters, stearic acids), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the compound is released over a period of time after administration. Controlled or sustained release compositions include formulation in lipophilic depots (e.g. fatty acids, waxes, oils). In another embodiment, the composition is an immediate release composition, i.e. a composition in which all of the compound is released immediately after administration.

In another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions, which contain an active component is well understood in the art, for example by mixing, granulating, or tablet-forming processes. The active therapeutic ingredient is often mixed with excipients which are pharmaceutically acceptable and compatible with the active ingredient. For oral administration, the compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the compounds or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the compounds of this invention will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, this invention also provides a composition comprising two or more compounds of this invention, or polymorphs, isomers, hydrates, salts, N-oxides, etc., thereof. The present invention also relates to compositions and pharmaceutical compositions, which comprise a compound as herein described, alone or in combination with a progestin or estrogen, or in another embodiment, chemotherapeutic compound, osteogenic or myogenic compound, or other agents suitable for the applications as herein described. In one embodiment, the compositions of this invention will comprise a suitable carrier, diluent or salt.

In one embodiment, the methods of this invention may comprise administration of a compound of this invention at various dosages. In one embodiment, compound (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII), or any combination thereof is administered at a dosage of 1 mg. In another embodiment the compound is administered at a dosage of 0.01 mg, 0.03 mg, 0.1 mg, 0.3 mg, 0.75 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg.

In one embodiment, compounds (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII), or any combination thereof may be administered at various dosages. In one embodiment, the compound is administered at a dosage of 0.01-1 mg per day. In one embodiment, the compound is administered at a dosage of 0.1-200 mg per day. In one embodiment, the compound is administered at a dose of 0.1-10 mg per day, or in another embodiment, 0.1-25 mg per day, or in another embodiment, 0.1-50 mg per day, or in another embodiment, 0.3-15 mg per day, or in another embodiment, 0.3-30 mg per day, or in another embodiment, 0.5-25 mg per day, or in another embodiment, 0.5-50 mg per day, or in another embodiment, 0.75-15 mg per day, or in another embodiment, 0.75-60 mg per day, or in another embodiment, 1-5 mg per day, or in another embodiment, 1-20 mg per day, or in another embodiment, 3-15 mg per day, or in another embodiment, 30-50 mg, or in another embodiment, 30-75 mg per day, or in another embodiment 100-2000 mg per day.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention. In one embodiment, use of a compound as herein described or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound is being administered.

In one embodiment, a compound of this invention is administered in combination with another anti-cancer agent. In one embodiment, the anti-cancer agent is a monoclonal antibody. In some embodiments, the monoclonal antibodies are used for diagnosis, monitoring, or treatment of cancer. In one embodiment, monoclonal antibodies react against specific antigens on cancer cells. In one embodiment, the monoclonal antibody acts as a cancer cell receptor antagonist. In one embodiment, monoclonal antibodies enhance the patient's immune response. In one embodiment, monoclonal antibodies act against cell growth factors, thus blocking cancer cell growth. In one embodiment, anti-cancer monoclonal antibodies are conjugated or linked to anti-cancer drugs, radioisotopes, other biologic response modifiers, other toxins, or a combination thereof.

In another embodiment, the present invention includes compounds as herein described and compositions in which a compound of the invention is combined with an agent bound to a targeting agent, such as a monoclonal antibody (e.g., a murine or humanized monoclonal antibody). In one embodiment, the agent bound to a targeting agent is a cytotoxic agent. It will be appreciated that the latter combination may allow the introduction of cytotoxic agents into for example cancer cells with greater specificity. Thus, the active form of the cytotoxic agent (i.e., the free form) will be present only in cells targeted by the antibody. Of course, the compounds of the invention may also be combined with monoclonal antibodies that have therapeutic activity against cancer.

n one embodiment, a compound of this invention is administered in combination with a selective tyrosine kinase inhibitor. In some embodiments, the selective tyrosine kinase inhibitor inhibits catalytic sites of cancer promoting receptors thereby inhibiting tumor growth. In one embodiment, a selective tyrosine kinase inhibitor modulates growth factor signaling. In some embodiments, the selective tyrosine kinase inhibitor targets EGFR (ERB B/HER) family members. In one embodiment, the selective tyrosine kinase inhibitor is a BCR-ABL tyrosine kinase inhibitor. In one embodiment, the selective tyrosine kinase inhibitor is an epidermal growth factor receptor tyrosine kinase inhibitor. In one embodiment, the selective tyrosine kinase inhibitor is a vascular endothelial growth factor tyrosine kinase inhibitor. In one embodiment, the selective tyrosine kinase inhibitor is a Platelet Derived Growth Factor (PDGF) inhibitor.

In one embodiment, a compound of this invention is administered in combination with a cancer vaccine.

In one embodiment, a compound of this invention is administered in combination with an anti-cancer chemotherapeutic agent. In one embodiment, the anti-cancer chemotherapeutic agent is an alkylating agent, such as but not limited to cyclophosphamide. In one embodiment, the anti-cancer chemotherapeutic agent is a cytotoxic antibiotic such as but not limited to doxorubicin. In one embodiment, the anti-cancer chemotherapeutic agent is an antimetabolite, such as but not limited to methotrexate. In one embodiment, the anti-cancer chemotherapeutic agent is a vinca alkaloid, such as but not limited to vindesine. In some embodiments, the anti-cancer chemotherapeutic agents include platinum compounds such as but not limited to carboplatin, and taxanes such as docetaxel. In one embodiment, the anti-cancer chemotherapeutic agent is an aromatase inhibitor such as but not limited to anastrazole, exemestane, or letrozole.

n one embodiment, a compound of this invention is administered in combination with a Bax activity modulator such as alisol B acetate. In one embodiment, a compound of this invention is administered in combination with an angiotensin II receptor blocker such as losartan. In one embodiment, a compound of this invention is administered in combination with selenium, green tea cachecins, saw palmetto, lycopene, vitamin D, dietary soy, genistein or isoflavone.

In one embodiment, a compound of this invention is administered in combination with antineoplastic agents, such as alkylating agents, antibiotics, hormonal antineoplastics and antimetabolites. Examples of useful alkylating agents include alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophos-phoramide and trimethylolmelamine; nitrogen mustards such as chlorambucil, chlomaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, ranimustine, dacarbazine, mannomustine, mitobronitol, mitolactol and pipobroman. More such agents will be known to those having skill in the medicinal chemistry and oncology arts.

In some embodiments, other agents suitable for combination with compounds as herein described include protein synthesis inhibitors such as abrin, aurintricarboxylic acid, chloramphenicol, colicin E3, cycloheximide, diphtheria toxin, edeine A, emetine, erytlromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine, modeccin, neomycin, norvaline, pactamycin, paromomycine, puromycin, ricin, α-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine, β-1-D-arabinoside, amethopterin, aminopterin, 2-aminopurine, aphidicolin, 8-azaguanine, azaserine, 6-azauracil, 2'-azido-2'-deoxynuclio-sides, 5-bromodeoxycytidine, cytosine, β-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin and streptolydigin also can be combined with the compounds of the invention to provide pharmaceutical compositions.

In one embodiment, a compound of this invention is administered in combination with a vaccine for prostate cancer, Alisol B acetate, angiotensin II receptor blocker, or others known in the art. In one embodiment, a compound of this invention is administered in combination with an agent to decrease prostate (benign or malignant) hypertrophy, such as, for example, Selenium, green tea cachecins, saw palmetto, lycopene, vitamin D, dietary soy, genistein and isoflavone food product and others.

In one embodiment, the compound as herein described is administered in combination with an agent, which treats bone diseases, disorders or conditions, such as osteoporosis, bone fractures, etc., and this invention comprises methods of treating the same, by administering the compounds as herein described, alone or in combination with other agents.

In one embodiment, the methods provided herein and/or utilizing the compositions provided herein, are effective in reducing metastases to the bone, such as in terms of number of foci, the size of foci, or a combination thereof. In one embodiment, the subject suffers from prostate cancer.

A person skilled in the art would readily recognize that changes in the antineoplastic therapy according to the methods provided herein, utilizing the compositions provided herein may be conducted as a function of, or adjusted or varied as a function of, inter-alia, the severity of the underlying disease, the source of the underlying disease, the extent of the patients' pain and source of the patients' pain, as well as the stage of the disease. The therapeutic changes may include in certain embodiments, changes in the route of administration (e.g. intracavitarily, intraartiarly, intratumoraly etc.), forms of the compositions administered (e.g. tablets, elixirs, suspensions etc.), changes in dosage and the like. Each of these changes is well recognized in the art and is encompassed by the embodiments provided herein.

In one embodiment, the present invention provides for the use of combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art.

Treatments of the Invention

In some embodiments, the compounds of this invention are useful in any application in which neoplasia or carcinogenesis is halted, modulated or altered in any way that is beneficial to a subject in need.

In some embodiments, this invention provides for the use of a compound of formula I-XXI, or any compound as herein described, or its prodrug, analog, isomer, metabolite, derivative, pharmaceutically acceptable salt, pharmaceutical product, polymorph, crystal, impurity, N-oxide, hydrate or any combination thereof, for treating, reducing the severity of, reducing the incidence of, or reducing pathogenesis of neoplasia or carcinogenesis in a subject. In another embodiment, the neoplasia comprises adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell lung cancer, non small cell lung cancer, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In some embodiments, this invention provides the use of a compound of formula I-XXI, or any compound as herein described, including an analog, derivative, isomer, metabolite, pharmaceutically acceptable salt, pharmaceutical product, polymorph, crystal, impurity, hydrate, N-oxide or any combination thereof, for treating, reducing the severity of, reducing the incidence of, or reducing pathogenesis of cancer. In one embodiment, the cancer comprises any cancer of soft tissue. In one embodiment the cancer comprises prostate cancer; bladder cancers; brain cancers; bone tumors, colon cancer, endometrial cancer, liver cancer, lung cancer, lymphatic cancer, kidney cancer, osteosarcoma cancer, ovarian cancer, pancreas cancer, penis cancer, skin cancer, thyroid cancer; and/or hormone-dependent cancers.

In one embodiment, the subject is male. In another embodiment, the subject is female. In some embodiments, while the methods as described herein may be useful for treating either males or females, females may respond more advantageously to administration of certain compounds, for certain methods, as described and exemplified herein.

In one embodiment, the subject suffers from a sarcoma. In another embodiment, the subject suffers from an adenocarcinoma, colon carcinoma, melanoma, breast carcinoma, leukemia, lymphoma, gastric carcinoma, glioblastoma, astrocytoma, bladder carcinoma, pleural mesothelioma, oat cell carcinoma or bronchogenic carcinoma. In one embodiment, "treating" refers to both therapeutic treatment and prophylactic or preventative measures, wherein the object is to prevent or lessen the targeted pathologic condition or disorder as described hereinabove. Thus, in one embodiment, treating may include suppressing, inhibiting, preventing, treating, or a combination thereof. Thus, in one embodiment, "treating" refers inter alia to increasing time to sustained progression, expediting remission, inducing remission, augmenting remission, speeding recovery, increasing efficacy of or decreasing resistance to alternative therapeutics, or a combination thereof. In one embodiment, "preventing" refers inter alia to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, the terms "treating" or "treatment" includes preventative as well as disorder remitative treatment. The terms "reducing", "suppressing" and "inhibiting" have their commonly understood meaning of lessening or decreasing, in another embodiment, or delaying, in another embodiment, or reducing, in another embodiment the incidence, severity or pathogenesis of a disease, disorder or condition. In embodiment, the term treatment refers to delayed progression of, prolonged remission of, reduced incidence of, or amelioration of symptoms associated with the disease, disorder or condition. In one embodiment, the terms "treating" "reducing", "suppressing" or "inhibiting" refer to a reduction in morbidity, mortality, or a combination thereof, in association with the indicated disease, disorder or condition. In one embodiment, the term "progression" refers to an increasing in scope or severity, advancing, growing or becoming worse. The term "recurrence" means, in another embodiment, the return of a disease after a remission. In one embodiment, the methods of treatment of the invention reduce the severity of the disease, or in another embodiment, symptoms associated with the disease, or in another embodiment, reduces the number of biomarkers expressed during disease.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer to, inter alia, a genetic profile or familial relationship which is associated with a trend or statistical increase in incidence, severity, etc. of the indicated disease. In some embodiments, the term term "predisposed to" is to be considered to refer to inter alia, a lifestyle which is associated with increased risk of the indicated disease. In some embodiments, the term "predisposed to" is to be considered to refer to inter alia, the presence of biomarkers which are associated with the indicated disease, for example, in cancer, the term "predisposed to" the cancer may comprise the presence of precancerous precursors for the indicated cancer.

In some embodiments, the term "reducing the pathogenesis" is to be understood to encompass reducing tissue damage, or organ damage associated with a particular disease, disorder or condition. In another embodiment, the term "reducing the pathogenesis" is to be understood to encompass reducing the incidence or severity of an associated disease, disorder or condition, with that in question. In another embodiment, the term "reducing the pathogenesis" is to be understood to encompass reducing the number of associated diseases, disorders or conditions with the indicated, or symptoms associated thereto.

The term "administering", in another embodiment, refers to bringing a subject in contact with a compound of the present invention. Administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, symptoms being treated are primary, while in another embodiment, symptoms are secondary. In one embodiment, "primary" refers to a symptom that is a direct result of neoplasia or carcinogenesis, while in one embodiment, "secondary" refers to a symptom that is derived from or consequent to a primary cause. In one embodiment, the compounds for use in the present invention treat primary or secondary symptoms or secondary complications related to neoplasia or carcinogenesis. In another embodiment, the compounds for use in the present invention treat primary or secondary symptoms or secondary complications related to neoplasia or carcinogenesis.

In another embodiment, "symptoms" may be any manifestation of a disease or pathological condition, comprising inflammation, swelling, fever, pain, bleeding, itching, runny nose, coughing, headache, migraine, dizziness, blurry vision, diarrhea, vomiting, constipation, gas, indigestion, etc.

Thus, in one embodiment of the present invention, the compounds for use in the present invention are directed towards the resolution of symptoms of a disease or disorder of neoplasia or carcinogenesis. In another embodiment, the compounds affect the pathogenesis underlying neoplasia or carcinogenesis.

In one embodiment, neoplasia or carcinogenesis may affect a cell, in one embodiment, a vertebrate cell, in another embodiment, a mammalian cell, and in another embodiment, a human cell. It is to be understood that compounds of the present invention may be efficacious in treating any cell type in which neoplasia or carcinogenesis is present or in which the causes of neoplasia or carcinogenesis may exert an effect. In one embodiment, a compound for use in the present invention may localize to or act on a specific cell type. In one embodiment, a compound for use in the present invention may be cytoprotective. In one embodiment a compound for use in the present invention may be inserted or partially inserted into a cell membrane. In another embodiment a compound for use in the present invention may be effective in treating a plurality of cell types.

In one embodiment of the present invention, the useful pharmacological properties of the compounds for use in the present invention, some of which are described hereinabove, may be applied for clinical use, and disclosed herein as methods for the prevention or treatment of a disease. The biological basis of these methods may be readily demonstrated by standard cellular and animal models of disease.

In one embodiment, the pharmacological activities of compounds for use in the present invention, including membrane stabilization, anti-inflammation, anti-oxidant action, and attenuation of chemokine levels, may contribute to a treated cell's resistance to neoplasia or carcinogenesis. In one embodiment, cell membrane stabilization may ameliorate or prevent tissue injury arising in the course of an intestinal disease. In another embodiment, anti-oxidant action may limit oxidative damage to cell and blood components arising in the course of an intestinal disease. In another embodiment, attenuation of chemokine levels may attenuate physiological reactions to stress that arise in the course of an intestinal disease.

In one embodiment of the invention, the compounds for use in the present invention described herein can be used to treat disease, through amelioration, or prevention, of tissue injury arising in the course of pathological disease states by stabilizing cell membranes; limiting oxidative damage to cell and blood components; or attenuating physiological reactions to stress, as expressed in elevated chemokine levels.

In one embodiment, methods of the present invention involve treating a subject by inter alia controlling the expression, production, and activity of phospholipases such as PLA2; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxidants, oxygen radicals and nitric oxide; protection of cells, tissues, and plasma lipoproteins from damaging agents, such as reactive oxygen species (ROS) and phospholipases; controlling the expression, production, and activity of cytokines, chemokines and interleukins; anti-oxidant therapy; anti-endotoxin therapy or any combination thereof.

In one embodiment of the invention, the term "controlling" refers to inhibiting the production and action of the above mentioned factors in order to maintain their activity at the normal basal level and suppress their activation in pathological conditions.

It will be appreciated by one skilled in the art that the compounds characterized by the structures (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII), or any combination thereof may be administered according to any regimen, at any dosage, to suit a particular application, for example cancer type or cancer stage, or a particular subject, for example, male versus female, or for example, in consideration of the age and lifestyle choice of the subject. In some embodiments, such varied regimens are a function of the presence of preneoplastic lesions or frank neoplasia, or in some embodiments, the occurrence of metastasis.

Without further elaboration, it is believed that one skilled in the art can, using the preceding description, utilize the present invention to its fullest extent. The following preferred specific embodiments are, therefore, to be construed as merely illustrative, and not limiting the remainder of the disclosure in any way whatsoever.

EXAMPLES

Material and Methods

Compounds

Porcine pancreatic and Crotalus atrox $PLA_2$s were purchased from Sigma-Aldrich, St. Louis, Mo., USA. Hyaluronic acid-N-conjugated phosphatidyl-ethanolamine (HyPE, M.W. cr. 50 kD), was synthesized in the laboratory of S. Yedgar (Dan, P., et al. Biochemistry, 37, 6199-204 (1998); Beck, G., et al. Crit. Care Med, 31, 2015-21 (2003); Offer, S., et al. Am J Physiol Lung Cell Mol Physiol, 288, L523-9 (2005)).

Cell Culture

Human fibrosarcoma HT-1080 cells (CCL 121, ATCC, Rockville Md.) were maintained in DMEM supplemented with calf serum, 10%. Glutamine, pyruvate, non-essential amino acids, vitamins and antibiotics (Biological Industries, Kibbutz Beth HaEmek, Israel) were added as additional supplements.

Determination of Basement Membrane Invasiveness

Boyden chamber chemoinvasion assays were performed as previously described (Reich, R., M. et al. Clin Exp Metastasis, 13, 134-40 (1995)). Matrigel (reconstituted basement membrane; 25 microgram) was dried on a polycarbonated filter (Nucleopore® Polyester PVP free; Whatman International Ltd., UK). Fibroblast conditioned medium (obtained from confluent NIH-3T3 cells cultured in serum free DMEM) is used as the chemoattractant. Cells were harvested by brief exposure to 1 mM EDTA, washed with DMEM with 5 microgram collagen IV instead of Matrigel. This amount of collagen does not form a barrier to the migrating cells but rather an attachment substratum, and thus serves to measure cell motility.

Determination of MMP Activity (Zymography)

Sub-confluent cell cultures were incubated for 6/24 h in serum-free DMEM and the resulted supernatant was analyzed for collagenolytic activity. The collagenolytic activity was determined on a gelatin impregnated (1 mg/ml, Difco, USA), SDS-PAGE 8% gel, as previously described (Brassart, B., A. et al. Clin Exp Metastasis, 16, 489-500 (1998)). Containing 0.1% BSA, and added to the Boyden chambers (200, 000 cells). The chambers were incubated at 37° C. in humidified atmosphere of 5% $CO_2$/95% air for 6 h. The cells have traversed the Matrigel layer and attached to the lower surface of the filter and stained with Diff Quick (Dade Diagnostics, USA) and counted in five random fields. The mean of the counts was calculated and values are expressed in terms non-treated HT-1080 cells normalized to 100%.

Determination of Cell Chemotaxis

To rule out the possibility that the used inhibitors affect cell motility, chemotaxis evaluation was performed in a similar way to basement membrane invasion, with the exception that the filters are coated The bands were scanned (Epson Perfection 3200 Photo), and the intensity was determined with the NIH image 1.63 software. All values are expressed in terms in of untreated HT-1080 cells divided by the absorbance of the 3-(4,5-dimethylthiazol-2-yl)-2,5-diphenyltetrazolium bromide viability assay (MTT) [Kudo, I. & M. Murakami. Prostaglandins Other Lipid Mediat, 68-69, 3-58 (2002)] normalized to 100%.

Determination of Cell $PLA_2$ Activity

Confluent HT-1080 cells were metabolically labeled with either [$^3$H-AA] or [$^3$H-OA] (0.5 microCi/24 well plate) (Amersham Biosciences, UK), by overnight incubation with the radioactive fatty acid, then washed and the temporal release of the labeled fatty acid to the culture medium was monitored under the different treatments (Dan, P., et al. FEBS Lett, 383, 75-8 (1996)).

Determination of Exogenous $PLA_2$ Activity

Lipolytic activity of exogenous $PLA_2$ was determined by using 4N30BA (4-nitro-3-hydroxy-benzoic acid) (Sigma-Aldrich, St. Louis, Mo., USA) as a substrate. 10 microliter of $PLA_2$ [1 u/ml and 0.5u/ml] in Tris-HCl (pH=8 100 nM) was incubated with 190 microliter substrate solution (4N30BA resuspended in 150 mM KCl, 10 mM $CaCl_2$, 50mM Tris-HCl, pH=7.5) at room temperature for 1 h. The $PLA_2$ activity calculated as:

$$(A_{425nm} - A_{600nm})[OD_{425}/h] \times 0.07862 [\text{micromol}/OD_{425nm}] \times (1/\text{sample volume } [1/\text{ml}]).$$

Identification of Cell $sPLA_2$ and sPLA2 Receptor Expression

Cultured HT-1080 cells were assessed for the expression of mRNA for $sPLA_2$s. Total RNA was isolated from the cells using Tri-reagent (Sigma-Aldrich, St. Louis, Mo., USA). First strand cDNA was transcribed with M-MLV reverse transcriptase (RT) (Promega, Madison, USA). Each cDNA (5 microgram) was amplified in standard PCR reaction (30-35 cycles) containing ReddyMix™ Master Mix (1.5 mM $MgCl_2$) (ABgene®, UK) and 1.5mM oligonucleotide primers. The PCR was carried out in an Eppendorf Mastercycler with an initial 5 min denaturing at 94° C., followed by the sequence of denaturation (95° C., 30 s), annealing (50° C., 30 s), and extension (72° C., 2 min). A final extension of 20 min at 72° C. ended the reaction.

PCR analysis was performed on reversed transcribed mRNA using 5'CTT-GAC-TGC-AAG-ATG-AAA-CTC (SEQ ID NO: 1) as sense and 5'CTG-ACA-ATA-CTT-CTT-GGT-GTC (SEQ ID NO: 2) as antisense primers for $sPLA_2$-IB to give a 455 bp; 5'ACC-ATG-AAG-ACC-CTC-CTA-CT (SEQ ID NO: 3) as sense and 5'gaa-gag-ggg-act-cag-caa-cg (SEQ ID NO: 4) as antisense primers for $sPLA_2$-IIA to give a 449 bp; 5'CAG-GGG-GCT-TGC-TAG-AAC-TGA-A (SEQ ID NO: 5) as sense and 5'AAG-ACG-GTT-GTA-ACT-CCA-GAG-G (SEQ ID NO: 6) as antisense primers for $sPLA_2$-V to give a 329 bp; 5'CGC-GCC-CGG-CCA-AAT-AAA-ATA-A (SEQ ID NO: 7) as sense and 5'CAG-CGA-CGG-CAG-TAG-CAG-GAG-CAG (SEQ ID NO: 8) as antisense primers for $sPLA_2$-X to give a 410 bp; 5'CAG-AAG-AAA-GGC-AGT-TCT-GGA-TTG (SEQ ID NO: 9) as sense and 5'AAA-GCC-ACA-TCC-TGG-CTC-TGA-TT (SEQ ID NO: 10) as antisense for $sPLA_2$ receptor to give a 565 bp. The products were separated on 1.5% agarose gels.

Determination of $cPLA_2$ and its Phosphorylation

Cells (150,000) were plated on a 6-well plate. Twenty-four hours later, the culture medium was changed to a serum-free medium containing various treatments (intact or denatured porcine pancreatic $PLA_2$ (10 u/ml) with/without HyPE (10 M)). After incubation for 15 min, the cells were washed with cold PBS and lysed in 20 mM Tris-HCl (pH 7.5), 150 mM NaCl, 1 mM EDTA, 1 mM EGTA, 1% Triton X-100, 2.5 mM sodium pyrophosphate, 1 mM beta-Glycerophosphate, 1 mM sodium orthovanadate, 1 microgram/ml Leupeptin and 1 mM phenylmethylsulfonyl fluoride. Forty microgram of protein of each sample, under reducing conditions, were loaded on 8% SDS-PAGE. After electrophoresis, the proteins were transferred to PVDF membrane, Immobilone™-P (Millipore, USA). The blots were probed with the rabbit polyclonal phospho-cPLA$_2$ (Ser505) antibody (Cell Signaling technology, Inc., USA). Apparent molecular weight of the enzyme was 110 kDa. The membranes were probed with the respective antibodies overnight, followed by incubation with peroxidase-conjugated AffiniPure goat anti-rabbit IgG (1:5,000 dilution) (Jackson ImmunoResearch, West Grove, Pa.) for 1 h, and visualized using the ECL Western blot system (Pierce, Rockford, Ill.). Membranes were stripped, blocked, and then probed again with anti-cPLA$_2$ antibody (Cell Signaling technology, Inc., USA). The bands were scanned (Epson Perfection 3200 Photo), and the intensity was determined with the NIH image 1.63 software. All values are expressed in terms of untreated HT-1080 cells normalized to 100%.

Statistics

Statistical analysis was performed by student's t test and by Dunn test using ANOVA program.

Example 1

ExPLI Effects on Cancer Cell Invasiveness

The effect of an extracellular cell-impermeable PLA$_2$ inhibitor (ExPLI) on the invasion of HT-1080 fibrosarcoma cells through a reconstituted basement membrane was examined. HT-1080 cells were incubated for 24 h with HyPE, then washed, and challenged to cross through a Matrigel layer coated filter in a Boyden chamber.

FIG. 1 demonstrates that pre-treatment of the cancer cells with HyPE effectively inhibited cell invasiveness without affecting cell viability or motility (not shown). It should be emphasized that cells were treated with HyPE prior to interaction with Matrigel and no ExPLI was added during the invasion assay. In addition, as shown in FIG. 1, hyaluronic acid (HA) alone (without the lipidic portion of the ExPLI) did not affect cell invasiveness, demonstrating that the reduced invasiveness of cells after HyPE treatment is not due to ExPLI-exerted steric hindrance between the cells and the Matrigel.

Figure 2:
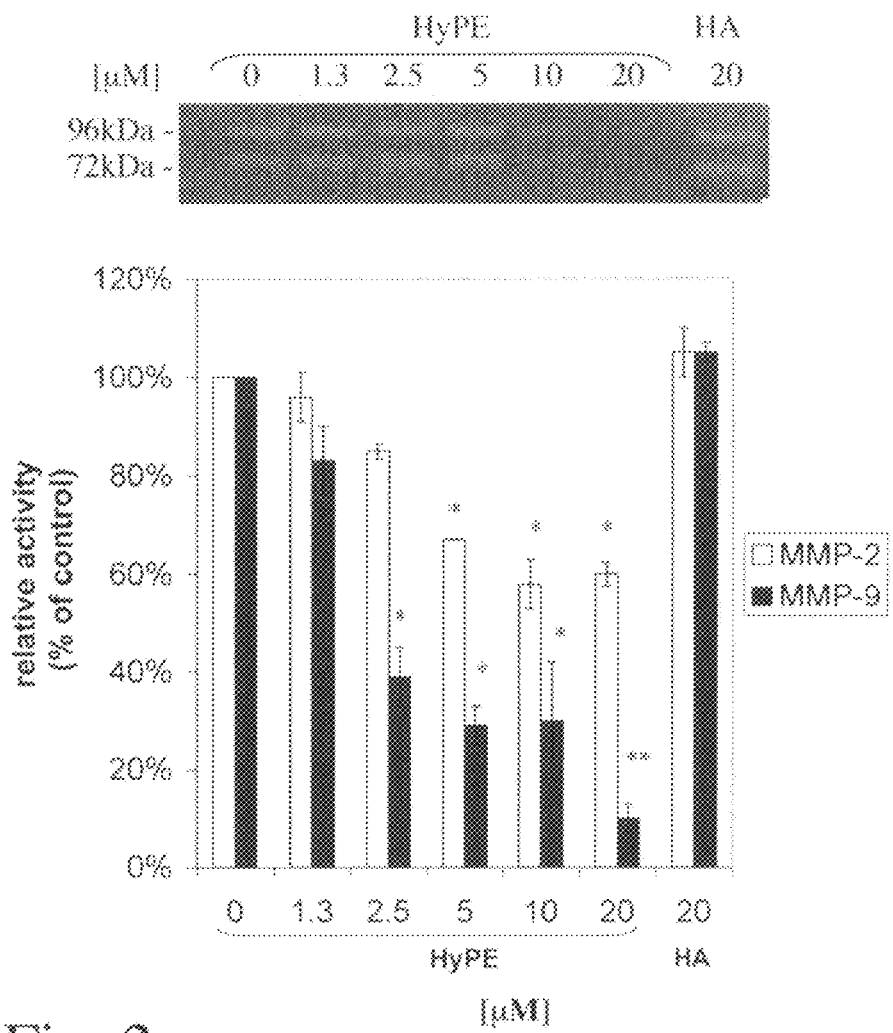
FIG. 2 describes the inhibition of MMP-2 and MMP-9 secretion from HT-1080 cells by sPLA$_2$ inhibitor. HT-1080 were incubated for 24 h with either HyPE or HA. The cultured medium was then collected and subjected to determination of MMP-2 (72 kDa) and MMP-9 (96 kDa) content by their collagenolytic activity, using zymography as described in Materials and methods. Each datum is Mean and SD for 4 replications (*, P less then 0.05, **, P less then 0.01).

Since the invasion of the basement membrane is dependent on the presence of collagen type IV degrading enzymes, the effect of HyPE effect on MMP-2 and MMP-9 secretion by the tumor cells was evaluated. Culture medium of HyPE-treated HT-1080 cells was collected and its collagenolytic activity was determined. FIG. 2 shows that the collagenolytic activity of both enzymes in the medium of HyPE-treated cells was reduced as a function of PLA$_2$ inhibitor concentration. Here too, treatment of cells with the GAG moiety alone did not inhibit MMP production.

Example 2

ExPLI Effects on PLA$_2$ Activity

Figure 3:
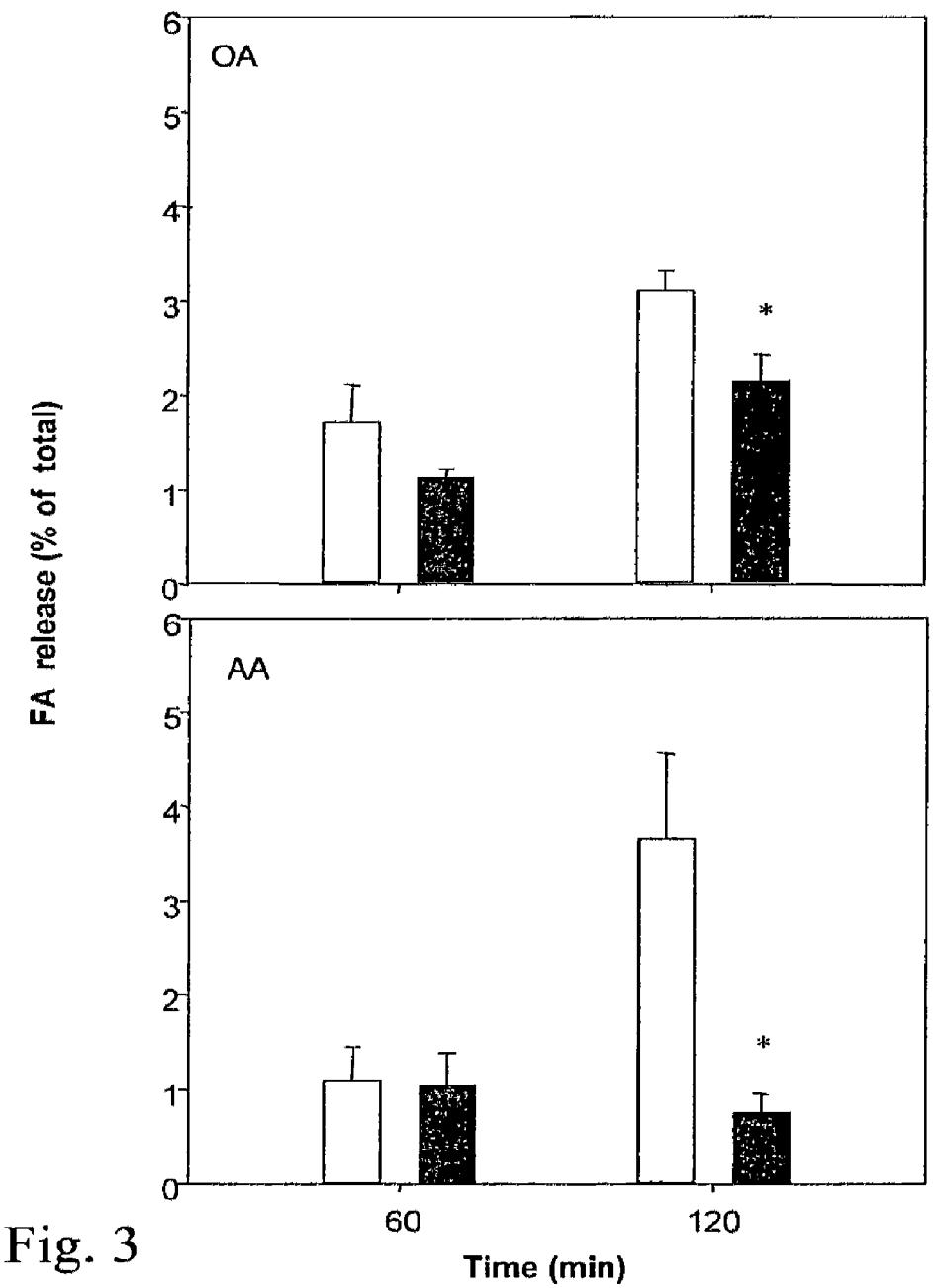
FIG. 3 describes the inhibition of PLA$_2$ activity by sPLA$_2$ inhibitor in HT-1080 cells. HT-1080 cells were metabolically labeled by overnight incubation with either $^3$H-arachidonic acid (AA) (lower panel) or $^3$H-oleic acid (OA) (upper panel), then washed and the release of the labeled AA or OA into the culture medium during the indicated time, in the absence (□) or presence (■) of HyPE was measured. Each datum is Mean and SD for 3 replications. (*, P less then 0.05).

The direct effect of HyPE on PLA$_2$ activity in HT-1080 cells was determined. Since cPLA$_2$ is specific to AA-carrying phospholipids, while sPLA$_2$ has no fatty acid preference, the cell membrane phospholipids were metabolically pre-labeled with either radioactively-labeled AA or oleic acid (OA), and the temporal fatty acid secretion to the culture medium was determined. FIG. 3 demonstrates that treatment of HT-1080 cells with an ExPLI inhibited the release of both AA and OA.

These findings together suggest that both sPLA$_2$ and cPLA$_2$ are involved in these processes, but since both activities are inhibited by the cell-impermeable inhibitor, it appears that they are controlled by sPLA$_2$.

Examination of the time course of the fatty acid release depicted in FIG. 3 shows that at 1 h, OA production, catalyzed by sPLA$_2$, is higher than that of AA, while the reverse is observed at 2 h. In addition, AA production is significantly enhanced at 2 h, while that of OA is relatively higher at 1 h. Moreover, at both time points, treatment with sPLA$_2$ inhibitor suppressed AA production to the level of the control, untreated cells. This may suggest that in HT-1080 cells the activity of sPLA$_2$ (producing both OA and AA) precedes that of cPLA$_2$ (producing only AA), and raises the possibility that cPLA$_2$ is activated subsequent to sPLA$_2$ action.

Figure 4:
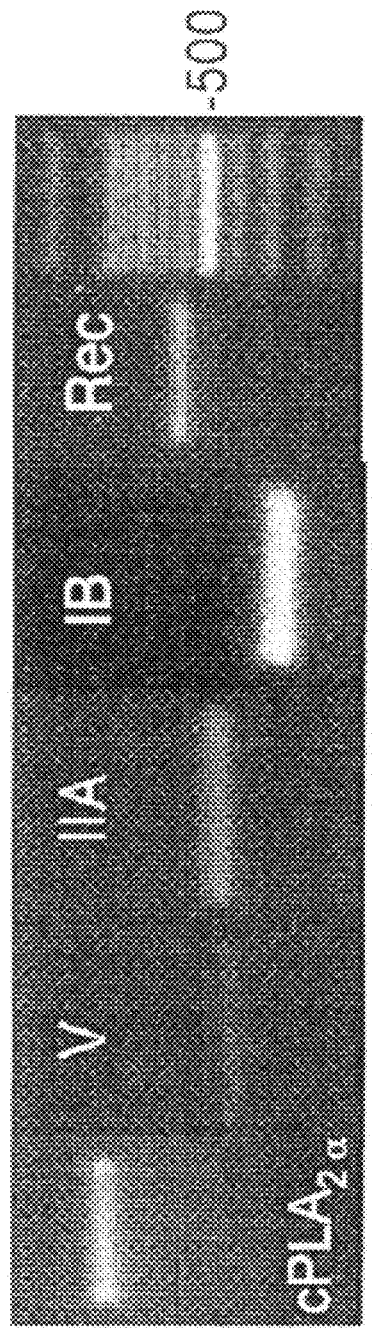
FIG. 4 shows the expression of PLA$_2$s and PLA$_2$ receptor by HT-1080 cells. mRNA expression of the indicated PLA$_2$ was determined by RT-PCR using the primers described in Materials and methods. The figures depicts RT-PCR of cPLA$_2$, (988 bp); sPLA$_2$ Types V, IIA and IB (329 bp, 449 bp and 243 bp respectively); and M-Type sPLA$_2$ receptor (Rec, 565 bp).

As noted above, sPLA$_2$ may act as a lipolytic enzyme and/or as a receptor ligand. RT-PCR was used to determine sPLA$_2$ types that are expressed in the HT-1080 cells. Two receptor-ligand sPLA$_2$s reported to act via M-type receptors, specifically IB and X, and two sPLA$_2$s that act mainly as lipolytic enzymes, specifically IIA and V were investigated. Human HT-1080 fibrosarcoma cells express sPLA$_2$-IB, sPLA$_2$-IIA and sPLA$_2$-V as shown in FIG. 4. The cytosolic cPLA$_2$-IV alpha was identified as well. FIG. 4 also shows that HT-1080 cells express the receptor to sPLA$_2$-IB, thus implying the presence of all the components required for a PLA$_2$-mediated cell signaling.

Figure 5:
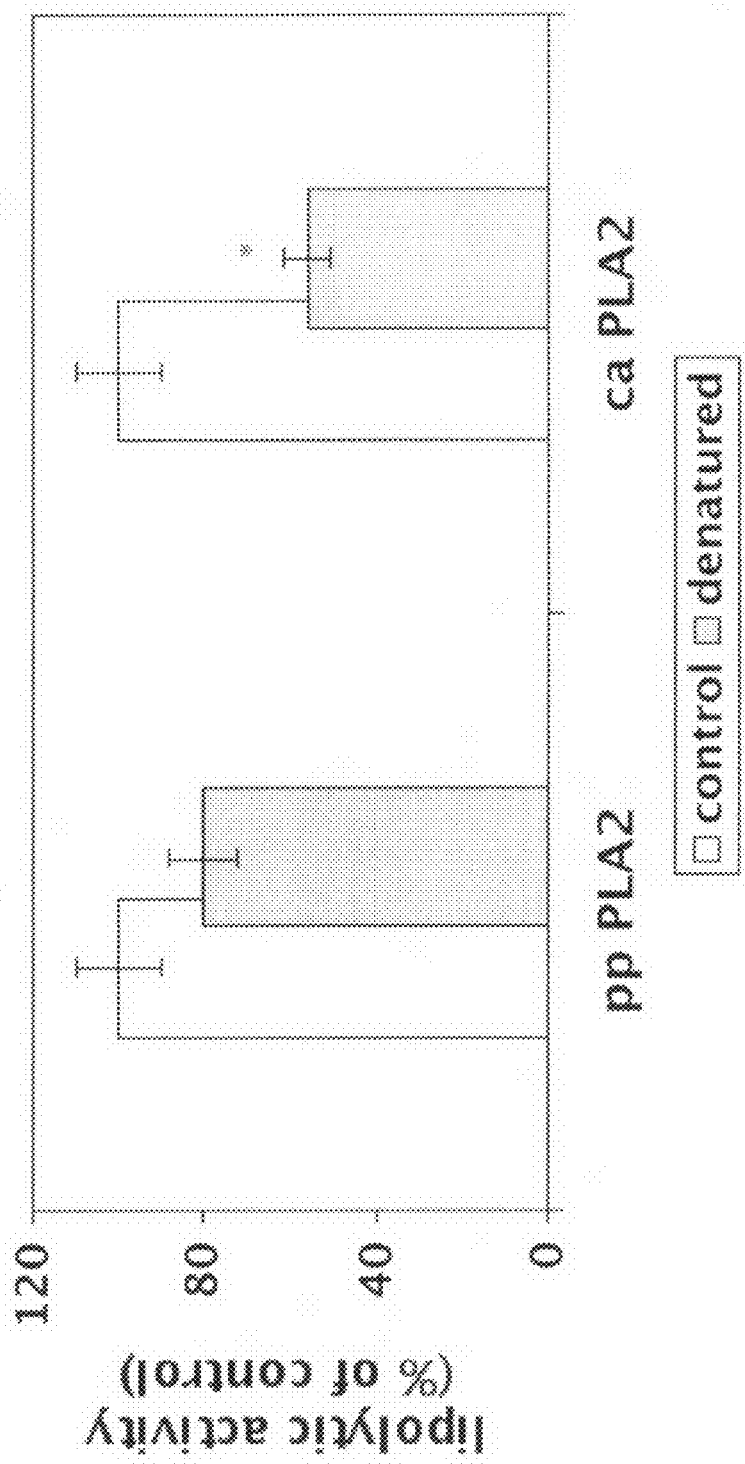
FIG. 5 shows the effect of heat inactivation on lipolytic activity of porcine pancreatic and crotalus atrox sPLA$_2$s (pp-PLA$_2$ and caPLA$_2$, respectively). The enzymes were denatured by heating at 95° C. for 15 min, and their lipolytic capacity was determined by their ability to hydrolyze 4N3OBA, as described in Materials and methods. Each datum is Mean and SD for 3 replications. (*, P less then 0.05).
Figure 6:
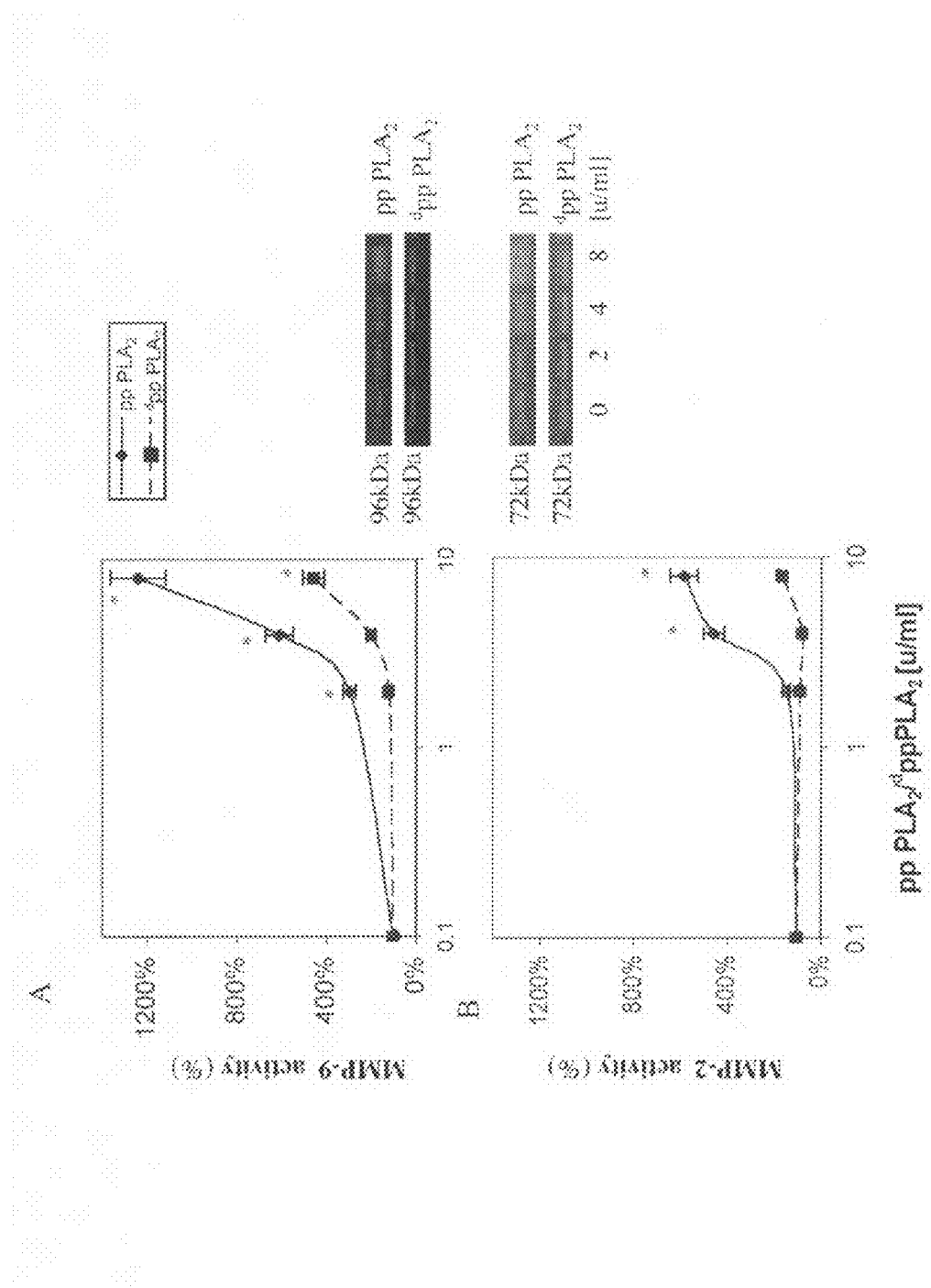
FIG. 6 demonstrates the effect of heat inactivation of ppPLA$_2$ on its ability to induce MMP production. HT-1080 cells were treated with either intact or denatured ($^d$) ppPLA$_2$ for 6 h, and the secretion of MMP-9 (A) and MMP-2 (B) secreted to the culture medium was determined by zymography. Each datum is Mean and SD for 3 replications (*, P less then 0.01).

Exogenous sPLA$_2$ may act as a lipolytic enzyme, hydrolyzing cell membrane phospholipids, and also as receptor ligand, independent of its lipolytic activity. Both these activities may lead to cPLA$_2$ activation, as sPLA$_2$-produced lyso-phospholipids and receptor-mediated cell signaling lead to cPLA$_2$ phosphorylation, which is required for its activation. To differentiate between the two potential mechanisms for the activation of MMP production, exogenous sPLA$_2$s were subjected to boiling, which is expected to inactivate their lipolytic activity, and MMP production by HT-1080 was determined following treatment with the native and boiled sPLA$_2$s. Two commercially-available sPLA$_2$s were employed; porcine pancreatic (Type-IB), for which HT-1080 cells express a receptor, and Crotalos atrox (Type-IIA) for which HT-1080 cells has no receptor. As shown in FIG. 5, boiling considerably suppressed the lipolytic activity of Type-IIA PLA$_2$, but had a small inhibitory effect on that of Type-IB (about 20%). On the other hand, production of both MMP-2 and MMP-9 was elevated by Type-IB PLA$_2$, in a concentration-dependent manner, as shown in FIG. 6. However, heating impaired the enzyme-receptor recognition, as heat-inactivation of sPLA$_2$-IB considerably suppressed its capacity to induce MMP production (to a much larger extent than the boiling effect on its lipolytic activity). MMP production was not affected by sPLA$_2$-IIA (not shown), nor was it attenuated by its heat inactivation, which inhibited its lipolytic activity (FIG. 5). These findings suggest that the induction of MMP production by sPLA$_2$ is mainly by a receptor-mediated process, rather than phospholipid hydrolysis-dependent.

Figure 7:
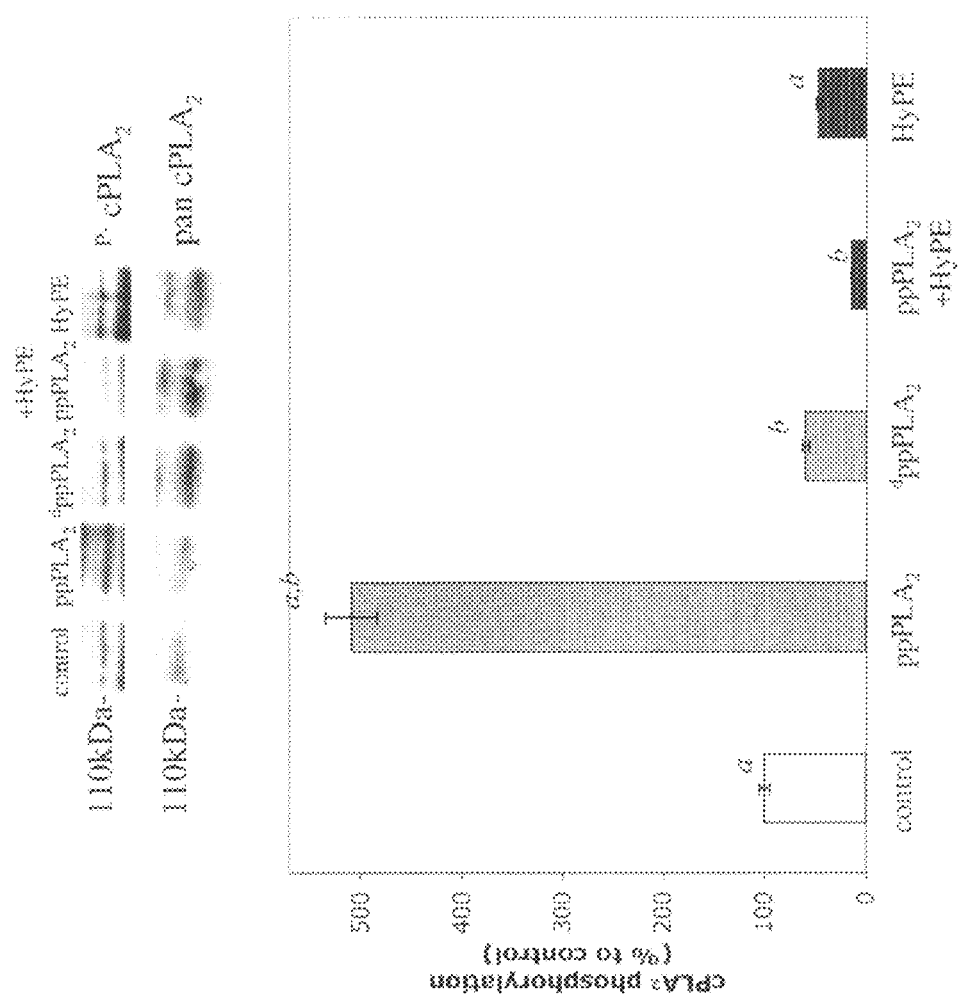
FIG. 7 presents cPLA$_2$ phosphorylation by ppPLA$_2$ and its suppression by heat inactivation or sPLA$_2$ inhibitor. HT-1080 cells were treated with ppPLA$_2$ in the absence (□) or presence (■) of HyPE, or with denatured ppPLA$_2$ for 15 min prior to protein isolation. The extent of cPLA$_2$ phosphorylation was determined by Western blot analysis with specific antibody directed against cPLA$_2$ phosphorylated on Ser505 and with specific antibody directed against the total (phosphorylated and non-phosphorylated) cPLA$_2$. Each datum is Mean and SD for 2 replications (a, b, P less then 0.05).

The present study supports findings that AA-derived eicosanoids are required for MMP production by the concomitant production of MMP and AA and inhibition of MMP secretion by the ExPLI (FIGS. 2 and 3). Since sPLA$_2$-dependent lipolysis does not contribute significantly to MMP production, one would assume that the required AA is provided by cPLA$_2$. This enzyme can be activated by phosphorylation that is induced by sPLA$_2$ receptor-mediated signaling, as has been previously reported for IB-sPLA$_2$. To examine this possibility in the present system, the phosphorylation status of cPLA$_2$ by native and heat-inactivated types IB and IIA sPLA$_2$ was assessed, and its inhibition by ExPLI. As shown in FIG. 7, sPLA$_2$-IB strongly enhanced cPLA$_2$ phosphorylation, and this was reduced to the basal level by heat inactivation of the enzyme or treatment with ExPLI. At the same time, sPLA$_2$-IIA did not lead to any cPLA$_2$ phosphorylation (not shown).

Figure 8:
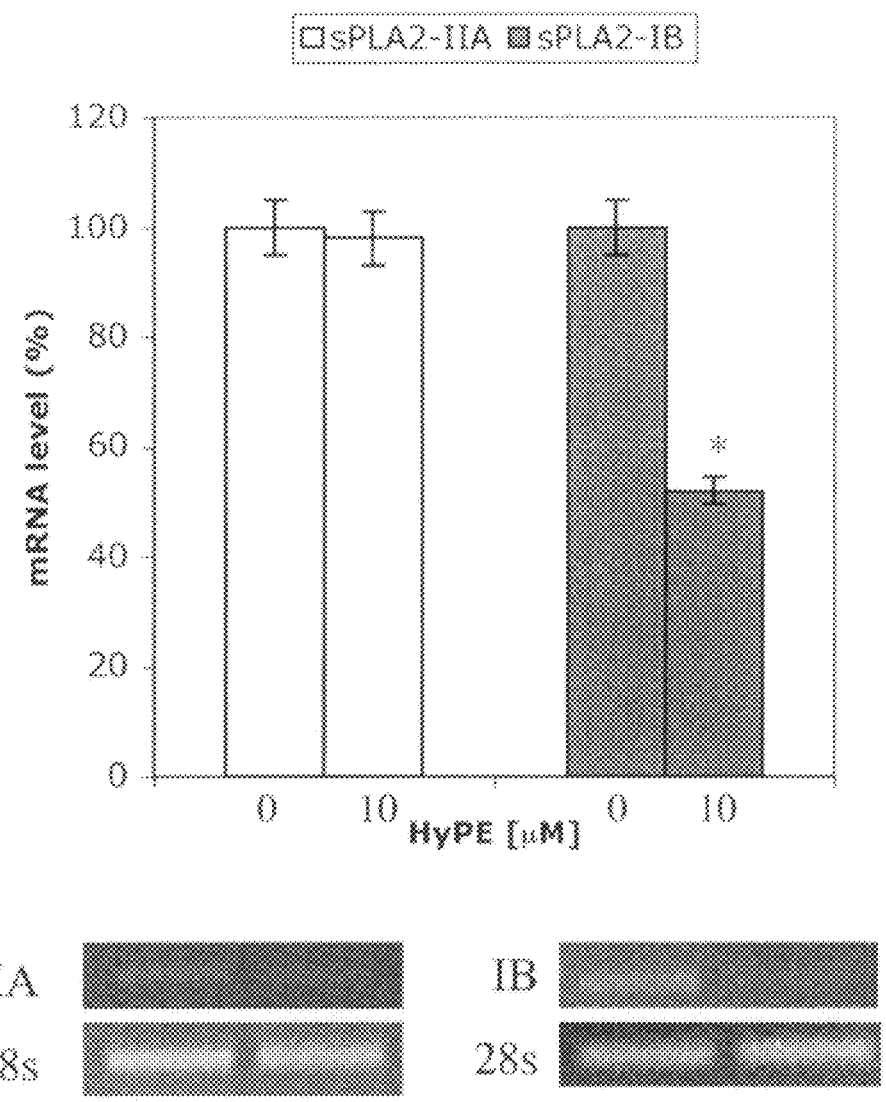
FIG. 8 describes the effect of HyPE on expression of sPLA$_2$ Types IIA and IB by HT-1080 cells. HT-1080 cells were treated for 24 h in the absence or presence of HyPE (10 microM) prior to RNA extraction. The expression of sPLA$_2$-IB and IIA in these cells were analyzed by RT-PCR using the primers described in Methods. Sample loading was verified by 28s expression. Each datum is Mean and SD for 3 replications (*, P less then 0.05).
Figure 9:
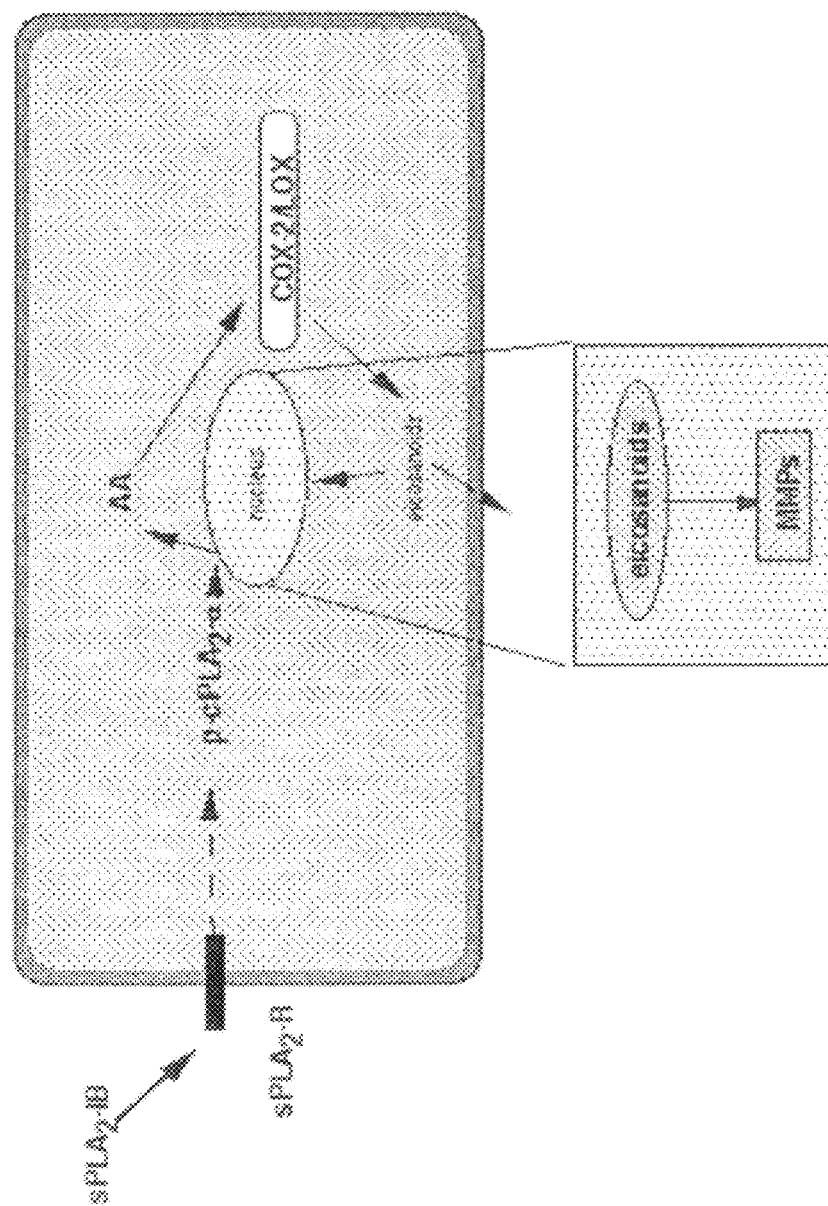
FIG. 9 presents a schematic describing the cascade involved in sPLA$_2$-IB-induced MMP activity. Working hypothesis. sPLA$_2$ binds to a membranal receptor and activates intracellular cPLA$_2$. cPLA$_2$ in its turn, releases AA that is converted into eicosanoids. sPLA$_2$-induced eicosanoids eventually induce MMP expression.

To further elaborate on the specific involvement of IB-PLA$_2$ in induction of MMP production, the ExPLI effect on PLA$_2$ mRNA expression was determined, using RT-PCR. As shown in FIG. 8, treatment of HT-1080 cells with ExPLI had no effect of IIA-PLA$_2$ expression, but considerably reduced (by 50%) the expression of PLA$_2$-IB, concomitantly with the above shown inhibition of cell invasiveness (FIG. 1), MMP production (FIG. 2) and cPLA$_2$ phosphorylation (FIG. 6).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of reducing the severity of neoplasia, or treating neoplasia in a subject suffering from a sarcoma comprising the step of administering to said subject suffering from a sarcoma a compound represented by the structure of the general formula (I):

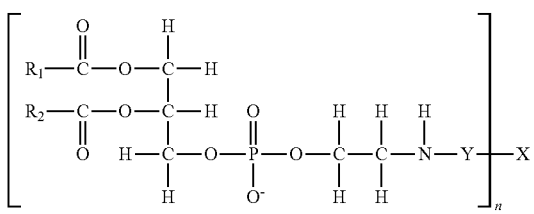

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms, wherein said spacer comprises —CO-alkylene-NH—, —CO-alkylene-CO— or a combination thereof;

wherein if Y is nothing the phospholipid moiety is directly linked to X via an amide bond and if Y is a spacer group, the spacer group is directly linked to X via an amide or an ester bond and to the phosphoethanolamine moiety via an amide bond;

X is hyaluronic acid, wherein the sugar rings of the glycosaminoglycan are intact; and n is a number from 1 to 1000;

and/or a pharmaceutically acceptable salt or a pharmaceutical product thereof.

2. The method according to claim 1, wherein $R_1$ and $R_2$ are both palmitoyl moieties.

3. The method according to claim 1, wherein $R_1$ and $R_2$ are both myristoyl moieties.

4. A method of reducing the severity of or pathogenesis of cancer metastasis in a subject suffering from a sarcoma, comprising the step of administering to said subject suffering from a sarcoma a compound represented by the structure of the general formula (I):

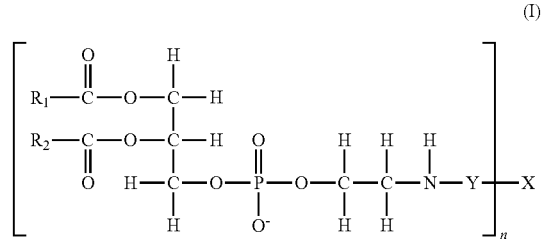

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms, wherein said spacer comprises —CO-alkylene-NH—, —CO-alkylene-CO— or a combination thereof;

wherein if Y is nothing the phospholipid moiety is directly linked to X via an amide bond and if Y is a spacer group, the spacer group is directly linked to X via an amide or an ester bond and to the phosphoethanolamine moiety via an amide bond;

X is hyaluronic acid, wherein the sugar rings of the glycosaminoglycan are intact; and n is a number from 1 to 1000;

and/or a pharmaceutically acceptable salt or a pharmaceutical product thereof.

5. The method according to claim 4, wherein $R_1$ and $R_2$ are both palmitoyl moieties.

6. The method according to claim 4, wherein $R_1$ and $R_2$ are both myristoyl moieties.

\* \* \* \* \*

SEQUENCE LISTING

```
<160> NUMBER OF SEQ ID NOS: 10

<210> SEQ ID NO 1
<211> LENGTH: 21
<212> TYPE: DNA
<213> ORGANISM: Homo sapiens

<400> SEQUENCE: 1
cttgactgca agatgaaact c                                            21

<210> SEQ ID NO 2
<211> LENGTH: 21
<212> TYPE: DNA
<213> ORGANISM: Homo sapiens

<400> SEQUENCE: 2
ctgacaatac ttcttggtgt c                                            21

<210> SEQ ID NO 3
<211> LENGTH: 20
<212> TYPE: DNA
<213> ORGANISM: Homo sapiens

<400> SEQUENCE: 3
accatgaaga ccctcctact                                              20

<210> SEQ ID NO 4
<211> LENGTH: 20
<212> TYPE: DNA
<213> ORGANISM: Homo sapiens

<400> SEQUENCE: 4
gaagagggga ctcagcaacg                                              20

<210> SEQ ID NO 5
<211> LENGTH: 22
<212> TYPE: DNA
<213> ORGANISM: Homo sapiens

<400> SEQUENCE: 5 caggggggctt gctagaactg aa                                          22

<210> SEQ ID NO 6
<211> LENGTH: 22
<212> TYPE: DNA
<213> ORGANISM: Homo sapiens

<400> SEQUENCE: 6
aagacggttg taactccaga gg                                           22

<210> SEQ ID NO 7
```

```
<211> LENGTH: 22
<212> TYPE: DNA
<213> ORGANISM: Homo sapiens

<400> SEQUENCE: 7
cgcgcccggc caaataaaat aa                                            22

<210> SEQ ID NO 8
<211> LENGTH: 24
<212> TYPE: DNA
<213> ORGANISM: Homo sapiens

<400> SEQUENCE: 8
cagcgacggc agtagcagga gcag                                          24

<210> SEQ ID NO 9
<211> LENGTH: 24
<212> TYPE: DNA
<213> ORGANISM: Homo sapiens

<400> SEQUENCE: 9
cagaagaaag gcagttctgg attg                                          24

<210> SEQ ID NO 10
<211> LENGTH: 23
<212> TYPE: DNA
<213> ORGANISM: Homo sapiens

<400> SEQUENCE: 10
aaagccacat cctggctctg att                                           23
```